United States Patent
Purchase, Jr. et al.

(10) Patent No.: US 6,541,521 B1
(45) Date of Patent: Apr. 1, 2003

(54) BENZENE BUTYRIC ACIDS AND THEIR DERIVATIVES AS INHIBITORS OF MATRIX METALLOPROTEINASES

(75) Inventors: Claude Forsey Purchase, Jr., Ann Arbor, MI (US); Bruce David Roth, Plymouth, MI (US); Andrew David White, Pinckney, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/351,549

(22) Filed: Jul. 12, 1999

(51) Int. Cl.$^7$ .................. A61K 31/195; C07C 207/00; C07C 229/00
(52) U.S. Cl. ...................... 514/567; 562/435; 562/438; 562/455
(58) Field of Search ................................ 562/455, 435, 562/438; 514/567, 532, 534, 538, 539; 560/21–23, 51, 54

(56) References Cited

U.S. PATENT DOCUMENTS

| | | | | |
|---|---|---|---|---|
| 3,978,124 | A | * 8/1976 | Fried et al. | 260/558 |
| 5,135,940 | A | * 8/1992 | Belanger et al. | 514/381 |
| 5,192,753 | A | 3/1993 | McGeer et al. | |
| 5,773,647 | A | * 6/1998 | Leone-Bay et al. | |
| 6,207,709 | B1 | * 3/2001 | Varsi et al. | 514/538 |

FOREIGN PATENT DOCUMENTS

| | | |
|---|---|---|
| EP | 0 757 037 A2 | 2/1997 |
| EP | 0 757 984 A1 | 2/1997 |
| GB | 1404022 | * 11/1972 |
| WO | WO 96/15096 | 5/1996 |
| WO | WO 96/17838 | * 6/1996 |
| WO | WO 97/27174 | 7/1997 |
| WO | WO 97/45402 | 12/1997 |
| WO | WO 97/49679 | 12/1997 |

OTHER PUBLICATIONS

Caplus abstract 90:137849 of DE 2727481, 1979.*
Caplus abstract 96:104272 of DE 3022176, 1982.*
Caplus abstract of Arzneim.–Forsch., vol. 30, No. 4A pp. 695–702, 1980.*
Caplus abstract of Helv. Chim. Acta, vol. 59, No. 6, pp. 2021–2031, 1976.*
Seki, T. et al "Studies on agents with vasodilator and beta–blocking activities" vol. 46, No. 1, pp. 84–96, 1998.*
Thyes, M., "6–Aryl–4,5–dihydro–3(2H)–pyridazinones" vol. 26, pp. 800–807, 1983.*
Sasaki, J., et al "Microbial oxidation KE–298 metabolities . . . " vol. 62, No. 6, pp. 1048–1054, 1998.*
Burpitt, B. E., et al "6–(Substitued phenyl)–5–methyl–4,5–dihydro–pyridazin–3(2H)–ones of medical interest" vol. 25, pp. 1689–1695, 1998.*
Abstract for Japanese PCT WO 97/27174 A.
Abstract for Japanese PCT WO 97/49697 A.

Aisen P.S., "Anti–inflammatory therapy for Alzheimer's disease," *Dementia*, 1995;9:173–82.
Andersen K., Launer L.J., Ott A., Hoes A.W., Breteler M.M.B., and Hofman A., "Do nonsteroidal anti–inflammatory drugs decrease the risk for Alzheimer's disease" The Rotterdam Study, *Neurology*, 1995;45:1441–5.
Andrews H.J., Plumpton T.A., Harper G.P., and Cawston T.E., "A synthetic peptide metalloproteinase inhibitor, but not Timp, prevents the breakdown of proteoglycan within cartilage in vitro", *Agents Actions*, 1992;37:145–154.
Armstrong P.W., Moe G.W., Howard R.J., Grima E.A., and Cruz T.F., "Structural remodeling in heart failure: Gelatinase induction," *Can. J. Cardiol.*, 1994;10;214–220.
Bagchus W.M., Hoedemaeker P.J., Rozing J., Bakker W.W., "Glomerulonephritis induced by monoclona anti–Thy 1.1 antibodies: A sequential histological and ultrastructural study in the rat," *Lab Invest.*, 1986;55:680–687.
Bendeck M.P., Zempo N., Clowes A.W., Galardy R.E., and Reidy M., "Smooth muscle cell migration and matrix metalloproteinase expression after arterial injury in the rat," *Circulation Research*, 1994;75:539–545.
Benelli R., Adatia R., Ensoli B., Stetler–Stevenson W.G., Santi L., and Albini A., "Inhibition of AIDS—Kaposi's sarcoma cell induced endothelial cell invasion by TIMP–2 and a synthetic peptide from the metalloproteinase propeptide: Implications for an anti–angiogenic therapy", *Oncology Research*, 1994;6:251–257.
Berge S.M. et al., "Pharmaceutical Salts," *J. of Pharma. Sci.*, 1977;66;1–19.
Breitner J.C.S., Gau B.A., Welsh K.A., et al., "Inverse association of anti–inflammatory treatments and Alzheimer's disease: Initial results of a co–twin control study," *Neurology*, 1994;44:227–32.

(List continued on next page.)

*Primary Examiner*—Paul J. Killos
*Assistant Examiner*—Leigh C. Maier
(74) *Attorney, Agent, or Firm*—Merchant & Gould P.C.

(57) ABSTRACT

Benzene butyric acid compounds and derivatives are described as well as methods for the preparation and pharmaceutical compositions of same, which are useful as inhibitors of matrix metalloproteinases, particularly gelatinase A, collagenase-3, and stromelysin-1 and for the treatment of multiple sclerosis, atherosclerotic plaque rupture, aortic aneurysm, heart failure, left ventricular dilation, restenosis, periodontal disease, corneal ulceration, treatment of burns, decubital ulcers, wound healing, cancer, inflammation, pain, arthritis, osteoporosis, renal disease, or other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

39 Claims, No Drawings

OTHER PUBLICATIONS

Breitner J.C.S., Welsh K.A., Helms M.J., et al., "Delayed onset of Alzheimer's disease with nonsteroidal anti–inflammatory and histamine H2 blocking drugs," *Neurobiol. Aging*, 1995;16:523–30.

Brown P.D., Levy A.T., Margulies I., Liotta L.A., Stetler-–Stevenson W.G., "Independent expression and cellular processing of $M_r$ 72,000 type IV collagenase and interstitial collagenase in human tumorigenic cell lines," *Cancer Res.*, 1990;50;6184–6191.

Brown S.I., Weller C.A., and Wasserman H.E., "Collagenolytic activity of alkali–burned corneas," *Arch. Ophthalmol.*, 1969;81:370–373.

Burns F.R., Stack M.S., Gray R.D., and Paterson C.A., "Inhibition of purified collagenase from alkali–burned rabbit corneas", *Invest. Ophthalmol.*, 1989;30:1569–1575.

Canadian Study of Health and Aging, "Risk factors for Alzheimer's disease in Canada," *Neurology*, 1994;44:2073–80.

Child R.G., Osterberg A.C., Sloboda, A.E., and Tomcufcik, A.S., "Fenbufen, a New Anti–Inflammatory Analgesic: Synthesis and Structure–Activity Relationships of Analogs," *Journal of Pharmaceutical Sciences*, 1977;66:4:466–76.

Clark R.K., Lee E.V., Fish C.J., et al., "Development of tissue damage, inflammation and resolution following stroke: an immunohistochemical and quantitative planimetric study," *Brain Res. Bull.*, 1993;31:565–72.

Davies et al., "A synthetic matrix metalloproteinase inhibitor decreases tumor burden and prolongs survival of mice bearing human ovarian carcinoma xenografts", *Cancer Res.*, 1993;53:2087–2091.

Davies M. et al., "Proteinases and glomerular matrix turnover," *Kidney Int.*, 1992;41:671–678.

DeClerck Y.A., Perez N., Shimada H., Boone T.C., Langley K.E., and Taylor S.M., Freije J.M., Diez–Itza I., Balbin M., Sanchez L.M., Blasco R., Tolivia J., and Lopez–Otin C., "Molecular cloning and expression of collagenase–3, a novel human matrix metalloproteinase produced by breast carcinomas", *J. Biol. Chem.*, 1994;269:16766–16773.

Ellis A.J., Curry V.A., Powell E.K., and Cawston T.E., "The prevention of collagen breakdown in bovine nasal cartilage by TIMP, TIMP–2 and low molecular weight synthetic inhibitor", *Biochem. Biophys. Res. Commun.*, 1994;201:94–101.

Galis Z.S., Sukhova G.K., Lark M.W., and Libby P., "Increased expression of matrix metalloproteinases and matrix degarding activity in vulnerable regions of human atherosclerotic plaques," *J. Clin. Invest.*, 1994;94:2493–2503.

Gendelman H.E. and Tardieu M., "Macrophages/microglia and the pathophysiology of CNS injuries in AIDS," *J. Leukocyte Biol.*, 1994;56:387–8.

Gijbels et al., "Reversal of experimental autoimmune encephalomyelitis with a hydroxamate inhibitor of matrix metalloproteases", *J. Clin. Invest.*, 1994;94:2177–2182.

Giulian D. and Vaca K., "Inflammatory glia mediate delayed neuronal damage after ischemia in the central nervous system," *Stroke*, 1993;24(Suppl 12):184–90.

Grams F. et al., "X–ray structures of human neutrophil collagenase complexed with peptide hydroxyamate and peptide thiol inhibitors. Implications for substrate binding and rational drug design," *Eur. J. Biochem.*, 1995;228:830–841.

Hsmpel H. and Müller N., "Inflammatory and immunological mechanisms in Alzheimer's disease," *DN&P*, 1995;8:599–608.

Henney A.M., Wakeley P.R., Davies M.J., Foster K., Hembry R., Murphy G., and Humphries S., "Localization of stromelysin gene expression in atherosclerotic plaques by in situ hybridization," *Proc. Nat'l. Acad. Sci.*, 1991;88:8154–8158.

Kitamura M. et al., "Gene transfer of metalloproteinase transin induces aberrant behaviour of cultured mesangial cells," *Kidney Int.*, 1994;45:1580–1586.

Lee T.H., Hamilton M.A., Stevenson L.W., Moriguchi J.D., Fonarow G.C., Child J.S., Laks H., and Walden J.A., "Impact of left ventricular size on the survival in advanced heart faliure," *Am. J. Cardiol.*, 1993;72:672–676.

Leigh P.N., "Pathogenic mechanisms in amyotrophic lateral sclerosis and other motor neuron disorders". In: Calne D.B., ed., Neurodegenerative Diseases, W.B. Saunders Company, 1994:473–88.

Lovette D.H., Johnson R.J., Marti H.P., Martin J., Davies M., Couser W.G., "Structural characterization of the mesangial cell type IV collagenase end enhanced expression in a model on immune complex mediated glomerulonephritis," *Am. J. Pathol.*, 1992;141:85–98.

Lucca U., Tettamanti M., Forloni G., and Spagnoli A., "Nonsteroidal anti–inflammatory drug use in Alzheimer's disease," *Biol. Psychiatry*, 1994;36:854–66.

Mandybur T.I. and Balko G., "Cerebral amyloid angiopathy with granulomatous angiitis ameliorated by steroid–cytoxan treatment," *Clin. Neuropharm.*, 1992;15:241–7.

Marti H.P. et al., "Homology cloning of rat 72 kDa type IV collagenase: Cytokine and second–messenger inducibility in mesangial cells," *Biochem. J.*, 1993;291:441–446.

Marti H.P. et al., "Transforming growth factor–β1 stimulates glomerular mesangial cell synthesis of the 72 kDa type IV collagenase," *Am. J. Pathol.*, 1994;144:82–94.

Martin J. et al., "Enhancement of glomerular mesangial cell neutral proteinase secretion by macrophages: role of interleukin $1^1$," *J. Immunol.*, 1986;317:525–529.

Martin R. and McFarland H.F., "Immunological aspects of experimental allergic encephalomyelitis and multiple sclerosis," *Crit. Rev. Clin. Lab. Sci.*, 1995;32:121–82.

Martin R., MacFarland H.F., amd MacFarlin D.E., "Immunological aspects of demyelinating diseases[1]," *Annual Rev. Immunol.*, 1992;10:153–87.

McGeer E.G. and McGeer P.L., "Neurodegeneration and the immune system". In: Calne D.B., ed. Neurodegenerative Diseases, W.B. Saunders Company, 1994:277–299.

McGeer P.L., Roger J., and McGeer E.G., "Neuroimmune mechanisms in Alzheimer disease pathogenesis," *Alzheimer Dis. Assoc. Disorders*, 1994;8:419–58.

McGeer P.L. and Rogers J., "Anti–inflammatory agents as a therapeutic approach to Alzheimer's disease," *Neurology*, 1992;42:447–9.

Melchiori A., Albili A., Ray J.M., and Stetler–Stevenson W.G., "Inhibition of tumor cell invasion by a highly conserved peptide sequence from the matrix metalloproteinase enzyme prosegment", *Cancer Res.*, 1992;52–2353–2356.

Monsky W.L., Kelly T., Lin C.–Y., Yeh Y., Stetler–Stevenson W.G., Mueller S.C., and Chen W.–T., "Binding and localization of $M_r$ 72,000 matrix metalloproteinase at cell surface invadopodia", *Cancer Res.*, 1993;53:3159–3164.

Overall C.M., Wiebkin O.W., and Thonard J.C., "Demonstrations of tissue collagenase activity in vivo and its relationship to inflammation severity in human gingiva," *J. Periodontal Res.*, 1987;22:81–88.

Patterson P.H., "Cytokines in Alzheimer's disease and multiple sclerosis," *Cur. Opion Neurobiol.*, 1995;5:642–646.

Pauly R.R., Passaniti A., Bilato C., Monticone R., Cheng L., Papadopoulos N., Gluzband Y.A., Smith L., Weinstein C., Lakatta E., and Crow M.T., "Migration of cultured vascular smooth muscle cells through a basement membrane barrier requires type IV collagenase activity and is inhibited by cellular differentation," *Circulation Research*, 1994;75:41–54.

Ramanic A.M., and Madri J.A., "The Induction of 72–kDa Gelatinase in T Cells upon Adhesion to Endothelial Cells is VCAM–1 Dependent," *J. Cell Biology*, 1994;125:1165–1178.

Reddy H.K., Tyagi S.C., Tjaha I.E., Voelker D.J., Campbell S.E., and Weber K.T., "Activated myocardial collagenase in idiopathic dilated cardiomyopathy: a marker of dilatation and remodeling," *Clin. Res.*, 193;41–660A.

Rich J.B., Rasmusson D.X., Folstein M.F., et al., "Nonsteroidal anti–inflammatory drugs in Alzheimer's disease," *Neurology*, 1995;45;51–5.

Rogers J., Webster S., Lue L.F., et al., "Inflammation and Alzheimer's dieases pathogenesis", In: *Neurobiology of Aging*, 1996; 17;681–686.

Rothwell N.J. and Relton J.K., "Involvement of cytokines in acute neurodegeneration in the CNS," *Neurosci. Biobehav. Rev.*, 1993;17:217–27.

Saarialho–Kere U.K., Ulpu K., Pentland A.P., Birkedal–Hansen H., Parks W.C., and Welgus H.G., "Distinct Populations of Basal Keratinocytes Express Stromelysin–1 and Stromelysin–2 in Chronic Wounds," *J. Clin. Invest.*, 1994;94:79–88.

Sabbah H.N., Kono T., Stein P.D., Mancini G.B., and Goldstein S., "Left ventricular shapes changes during the course of evolving heart failure," *Am. J. Physiol.*, 1992;263:H266–270.

Sato H., Takino T., Okada Y., Cao J. Shinagawa A., Yamamoto E., and Seiki M., "A matrix metalloproteinase expressed on the surface of invasive tumour cells", *Nature*, 1994;370:61–65.

Strongin A.Y., Marmer B.L., Grant G.A., and Goldberg G.I., "Plasma membrane–dependent Activation of the 72–kDa type IV collagenase is prevented by complex formation with TIMP–2", *J. Biol. Chem.*, 1993;268:14033–14039.

Taraboletti G., Garofalo A., Belotti D., Drudis T., Borsotti P., Scanziani E., Brown P.D., and Giavazzi R., "Inhibition of angiogenesis and murine hemangioma growth by batimastat, a synthetic inhibitor of mixture metalloproproteinases", *Journal of the National Cancer Institute*, 1995;87:293.

Turck J. et al., "Matrix metalloproteinase 2 (gelatinase A) regulates glomerular mesangial dell proliferation and differentiation," *J. Biol. Chem.*, 1996;271:15074–15083.

Tyagi S.C., Reddy H.K., Voelker D., Tjara I.E., and Weber K.T., "Myocardial collegenase in falling human heart," *Clin. Res.*, 1993;41:681A.

Uitto V.J., Applegren R., and Robinson P.J., "Collagenase and neutral metallo–proteinase activity in extracts from inflamed human gingiva," *J. Periodontal Res.*, 1981;16:417–424.

Vincenti M.P. et al., "Using inhibitors of metalloproteinases to treat arthritis," *Arthritis Rheum.*, 1994;37:8:1115–1126.

Vine N. And Powell J.T., "Metalloproteinases in degenerative aortic diseases," *Clin. Sci.*, 1991;81;233–239.

Walakovits L.A., Moore V.L., Bhardwaj N., Gallick G.S., and Lark M.W., Detection of stromelysin and collagenase in synovial fluid from patients with rheumatoid arthritis and post–traumatic knee injury, *Arthritis Rheum.*, 1992;35:35–42.

Woessner J.F., "Matrix metalloproteinases and their inhibitors in connective tissue remodeling," *FASEB J.*, 1991;5:2145–2154.

Ye Q.–Z., Johnson L.L., Hupe D.J., and Baragi V., "Purification and Characterization of the Human Stromelysin Catalytic Domain Expressed in *Escherichia coli*," *Biochemistry*, 1992;31:11231–11235.

Ye Q.–Z., Johnson L.L., Yu A.E., and Hupe D., "Reconstructed 19 kDa catalytic domain of gelatinase A is an active proteinase," *Biochemistry*, 1995;34:4702–4708.

Ye Q.–Z, Johnson L.L., and Baragi V., "Gene synthesis and expression in *E. coli* for PUMP, a human matrix metalloproteinase," *Biochemical and Biophysical Research Communications*, 1992;186:143–149.

Zafarullah M. Pelletier J.P., Cloutier J.M., and Marcel–Pelletier J., "Elevated metalloproteinases and tissue inhibitor of metalloproteinase mRNA in human osteoarthritic synovia," *J. Rheumatol.*, 1993;20:693–697.

Caplus abstract of JP 0808664.*

Caplus abstract of J. Med. Chem., vol. 29, No. 9, pp. 1573–6, 1986.*

Caplus abstract of Bull. Chem. Soc. Jap., vol. 45, No. 9, pp. 2829–2834, 1972.*

* cited by examiner

BENZENE BUTYRIC ACIDS AND THEIR DERIVATIVES AS INHIBITORS OF MATRIX METALLOPROTEINASES

BACKGROUND OF THE INVENTION

The present invention relates to novel benzene butyric acid compounds and their derivatives useful as pharmaceutical agents, to methods for their production, to pharmaceutical compositions which include these compounds and a pharmaceutically acceptable carrier, and to pharmaceutical methods of treatment. The novel compounds of the present invention are inhibitors of matrix metalloproteinases, e.g., gelatinase A (MMP-2), collagenase-3 (MMP-13), and stromelysin-1 (MMP-3). More particularly, the novel compounds of the present invention are useful in the treatment of atherosclerotic plaque rupture, aortic aneurism, heart failure, left ventricular dilation, restenosis, periodontal disease, corneal ulceration, treatment of bums, decubital ulcers, wound repair, cancer, inflammation, pain, arthritis, osteoporosis, multiple sclerosis, renal disease, and other autoimmune or inflammatory disorders dependent on the tissue invasion of leukocytes or other activated migrating cells. Additionally, the compounds of the present invention are useful in the treatment of acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

Gelatinase A and stromelysin-1 are members of the matrix metalloproteinase (MMP) family (Woessner J. F., *FASEB J.*, 1991;5:2145–2154). Other members include fibroblast collagenase, neutrophil collagenase, gelatinase B (92 kDa gelatinase), stromelysin-2, stromelysin-3, matrilysin, collagenase 3 (Freije J. M., Diez-Itza I., Balbin M., Sanchez L. M., Blasco R., Tolivia J., and Lopez-Otin C., *J. Biol. Chem.*, 1994;269:16766–16773), and the newly discovered membrane-associated matrix metalloproteinases (Sato H., Takino T., Okada Y., Cao J., Shinagawa A., Yamamoto E., and Seiki M., *Nature*, 1994;370:61–65).

The catalytic zinc in matrix metalloproteinases is a focal point for inhibitor design. The modification of substrates by introducing chelating groups has generated potent inhibitors such as peptide hydroxymates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of an atherosclerotic plaque is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galis Z. S., Sukhova G. K., Lark M. W., and Libby P., "Increased expression of matrix metalloproteinases and matrix degrading activity in vulnerable regions of human atherosclerotic plaques," *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization," *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases," *Clin. Sci.*, 1991;81:233–239).

Heart failure arises from a number of diverse etiologies, but a common characteristic is cardiac dilation, which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure," *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy," *Clin. Res.*, 1993;41:660A; Tyagi S. C., Reddy H. K., Voelker D., Tjara I. E., and Weber K. T., "Myocardial collagenase in failing human heart," *Clin. Res.*, 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction," *Can. J. Cardiol.*, 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure," *Am. J. Physiol.*, 1992;263:H266–270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat," *Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSMCs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation," *Circulation Research*, 1994;75:41–54).

Collagenase and stromelysin activities have been demonstrated in fibroblasts isolated from inflamed gingiva (Uitto V. J., Applegren R., and Robinson P. J., "Collagenase and neutral metalloproteinase activity in extracts from inflamed human gingiva," *J. Periodontal Res.,* 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva," *J. Periodontal Res.,* 1987;22:81–88). Proteolytic degradation of extracellular matrix has been observed in corneal ulceration following alkali burns (Brown S. I., Weller C. A., and Wasserman H. E., "Collagenolytic activity of alkali burned corneas," *Arch. Ophthalmol.,* 1969;81:370–373). Thiol-containing peptides inhibit the collagenase isolated from alkali-burned rabbit corneas (Bums F. R., Stack M. S., Gray R. D., and Paterson C. A., *Invest. Ophthalmol.,* 1989;30:1569–1575).

Stromelysin is produced by basal keratinocytes in a variety of chronic ulcers (Saarialho-Kere U. K., Ulpu K., Pentland A. P., Birkedal-Hansen H., Parks W. O., and Welgus H. G., "Distinct Populations of Basal Keratinocytes Express Stromelysin-1 and Stromelysin-2 in Chronic Wounds," *J. Clin. Invest.,* 1994;94:79–88).

Stromelysin-1 mRNA and protein were detected in basal keratinocytes adjacent to but distal from the wound edge in what probably represents the sites of the proliferating epidermis. Stromelysin-1 may thus prevent the epidermis from healing.

Davies et al., (*Cancer Res.,* 1993;53:2087–2091) reported that a peptide hydroxymate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.,* 1992;52:2353–2356). The natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.,* 1992;52:701–708). Studies of human cancers have shown that gelatinase A is activated on the invasive tumor cell surface (Strongin A. Y., Marmer B. L., Grant G. A., and Goldberg G. I., *J. Biol. Chem.,* 1993;268:14033–14039) and is retained there through interaction with a receptor-like molecule (Monsky W. L., Kelly T., Lin C.-Y., Yeh Y., Stetler-Stevenson W. G., Mueller S. C., and Chen W.-T., *Cancer Res.,* 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute,* 1995;87:293 and Benelli R., Adatia R., Ensoli B., Stetler-Stevenson W. G., Santi L., and Albini A, *Oncology Research,* 1994;6:251–257).

Several investigators have demonstrated consistent elevation of stromelysin and collagenase in synovial fluids from osteo- and rheumatoid arthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury," *Arthritis Rheum.,* 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia," *J. Rheumatol.,* 1993;20:693–697). TIMP-1 and TIMP-2 prevented the formation of collagen fragments, but not proteoglycan fragments in both the bovine nasal and pig articular cartilage models for arthritis, while a synthetic peptide hydroxamate could prevent the formation of both fragments (Andrews H. J., Plumpton T. A., Harper G. P., and Cawston T. E., *Agents Actions,* 1992;37:147–154; Ellis A. J., Curry V. A., Powell E. K., and Cawston T. E., *Biochem. Biophys. Res. Commun.,* 1994;201:94–101).

Gijbels et al., (*J. Clin. Invest.,* 1994;94:2177–2182) recently described a peptide hydroxamate, GM600 1, that suppressed the development or reversed the clinical expression of experimental autoimmune encephalomyelitis (EAR) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M., and Madri J. A., "The Induction of 72-kDa Gelatinase in T Cells upon Adhesion to Endothelial Cells is VCAM-1 Dependent," *J. Cell Biology,* 1994; 125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Also, leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provide the basis for the expectation that an effective inhibitor of gelatinase A and/or stromelysin-1 would have value in the treatment of diseases involving disruption of extracellular matrix resulting in inflammation due to lymphocytic infiltration, inappropriate migration of metastatic or activated cells, or loss of structural integrity necessary for organ function.

Neuroinflammatory mechanisms are implicated in a broad range of acute and chronic neurodegenerative disorders, including stroke, head trauma, multiple sclerosis, and Alzheimer's disease, to name a few (McGeer E. G. and McGeer P. L., "Neurodegeneration and the immune system". In: Calne D. B., ed. Neurodegenerative Diseases, W. B. Saunders, 1994:277–300). Other disorders that may involve neuroinflammatory mechanisms include amyotrophic lateral sclerosis (Leigh P. N., "Pathogenic mechanisms in amyotrophic lateral sclerosis and other motor neuron disorders". In: Calne D. B., ed., Neurodegenerative Diseases, W. B. Saunders, 1994:473–88), cerebral amyloid angiopathy. (Mandybur T. I. and Balko G., "Cerebral amyloid angiopathy with granulomatous angiitis ameliorated by steroid-cytoxan treatment," *Clin. Neuropharm.,* 1992; 15:241–7), AIDS (Gendelman H. E. and Tardieu M., "Macrophages/microglia and the pathophysiology of CNS injuries in AIDS," *J. Leukocyte Biol.,* 1994;56:387–8), Parkinson's disease, Huntington's disease, prion diseases, and certain disorders involving the peripheral nervous system, such as myasthenia gravis and Duchenne's muscular dystrophy. Neuroinflammation, which occurs in response to brain injury or autoimmune disorders, has been shown to cause destruction of healthy tissue (Martin R., MacFarland H. F., and McFarlin D. E., "Immunological aspects of demyelinating diseases," *Annul Rev. Immunol.,* 1992; 10:153–87; Clark R. K., Lee E. V., Fish C. J., et al., "Development of tissue damage, inflammation and resolution following stroke: an immunohistochemical and quantitative planimetric study," *Brain Res. Bull.,* 1993;31:565–72; Giulian D. and Vaca K., "Inflammatory glia mediate delayed neuronal damage after ischemia in the central nervous system," Stroke, 1993;24(Suppl 12):184–90; Patterson P. H., "Cytokines in Alzheimer's disease and multiple sclerosis," Cur. Opinion Neurobiol., 1995;5:642–6; McGeer P. L., Rogers J., and McGeer E. G., "Neuroimmune mechanisms in Alzheimer disease pathogenesis," Alzheimer Dis. Assoc. Disorders, 1994;8:149–58; Martin R. and McFarland H. F., "Immunological aspects of experimental allergic encephalomyelitis and multiple sclerosis," Crit. Rev. Clin. Lab. Sci., 1995;32:121–82; Rogers J., Webster S., Lue L. F., et al., "Inflammation and Alzheimer's disease pathogenesis". In: Neurobiology of Aging, 1996;17:681–686; Rothwell N. J. and Relton J. K., "Involvement of cytokines in acute neurodegeneration in the CNS," Neurosci. Biobehav. Rev., 1993;17:217–27). The pathological profiles and clinical courses of these disorders differ widely, but they all have in common the participation of immune/inflammatory elements in the disease process. In particular, many neurodegenerative disorders are characterized by large numbers of reactive microglia in postmortem brain samples, indicative of an active inflammatory process (McGeer E. G. and McGeer P. L., supra., 1994).

Increasing attention is being directed toward inflammatory mechanisms in Alzheimer's disease. Several lines of evidence support the involvement of neuroinflammation in Alzheimer's disease: 1) There is a significant increase in inflammatory markers in the Alzheimer brain, including acute phase reactants, cytokines, complement proteins, and MHC molecules (McGeer et al., supra., 1994; Rogers et al., supra.); 2) There is evidence that β-amyloid induces neurodegenerative changes primarily through interactions with inflammatory molecules, and that inflammation alone is sufficient to induce neurodegeneration (Rogers et al., supra); and 3) Growing epidemiological data indicate that anti-inflammatory therapy can delay the onset and slow the progression of Alzheimer's disease (McGeer P. L. and Rogers J., "Anti-inflammatory agents as a therapeutic approach to Alzheimer's disease," Neurology, 1992;42:447–9; Canadian Study of Health and Aging, "Risk factors for Alzheimer's disease in Canada," Neurology, 1994;44:2073–80; Lucca U., Tettamanti M., Forloni G., and Spagnoli A., "Nonsteroidal antiinflammatory drug use in Alzheimer's disease," Biol. Psychiatry, 1994;36:854–66; Hampel H. and Müller N., "Inflammatory and immunological mechanisms in Alzheimer's disease," DN&P, 1995;8:599–608; Breitner J. C. S., Gau B. A., Welsh K. A., et al., "Inverse association of anti-inflammatory treatments and Alzheimer's disease: Initial results of a co-twin control study," Neurology, 1994;44:227–32; Breitner J. C. S., Welsh K. A., Helms M. J., et al., "Delayed onset of Alzheimer's disease with nonsteroidal anti-inflammatory and histamine H2 blocking drugs," Neurobiol. Aging, 1995;16:523–30; Andersen K., Launer L. J., Ott A., Hoes A. W., Breteler M. M. B., and Hofman A., "Do nonsteroidal anti-inflammatory drugs decrease the risk for Alzheimer's disease? The Rotterdam Study," Neurology, 1995;45:1441–5; Rich J. B., Rasmusson D. X., Folstein M. F., et al., "Nonsteroidal anti-inflammatory drugs in Alzheimer's disease," Neurology, 1995;45:51–5; Aisen P. S., "Anti-inflammatory therapy for Alzheimer's disease," Dementia, 1995;9:173–82; Rogers et al., supra). Chronic use of nonsteroidal anti-inflammatory drugs (NSAIDs), most commonly for the treatment of rheumatoid arthritis, decreases the probability of developing Alzheimer's disease, and there is reason to believe that other anti-inflammatory agents may also be effective, although direct evidence for the efficacy of such treatments is lacking (Hamper and Müller, supra., 1995). Furthermore, virtually all of the currently available compounds, which include corticosteroids, NSAIDs, antimalarial drugs, and colchicine, have serious drawbacks that make them undesirable in the treatment of chronic disorders. Glucocorticoids, which are in wide clinical use as anti-inflammatory/immunosuppressive drugs, can be directly neurotoxic and also are toxic to systemic organs at moderate to high doses. NSAIDs have gastrointestinal and renal side effects that obviate long-term use in most people, and few of them cross the blood-brain barrier in significant amounts. The toxic properties of chloroquine compounds and colchicine also are well known. An anti-inflammatory drug that is well-tolerated by patients and that crosses the blood-brain barrier has significant advantages for the treatment of acute and chronic degenerative diseases of the central nervous system.

Normal kidney function is dependent on the maintenance of tissues constructed from differentiated and highly specialized renal cells which are in a dynamic balance with their surrounding extracellular matrix (ECM) components (Davies M. et al., "Proteinases and glomerular matrix turnover," Kidney Int., 1992;41:671–678). Effective glomerular filtration requires that a semi-permeable glomerular basement membrane (GBM) composed of collagens, fibronectin, enactin, laminin and proteoglycans is maintained. A structural equilibrium is achieved by balancing the continued deposition of ECM proteins with their degradation by specific metalloproteinases (MMP). The MMP belong to a supergene family of zinc endopeptidases (Woessner J. F., "Matrix metalloproteinases and their inhibitors in connective tissue remodelling," FASEB J., 1991;5:2145–2154). These proteins are first secreted as proenzymes and are subsequently activated in the extracellular space. These proteinases are in turn subject to counter balancing regulation of their activity by naturally occurring inhibitors referred to as TIMPs (tissue inhibitors of metalloproteinases).

Deficiency or defects in any component of the filtration barrier may have catastrophic consequences for longer term renal function. For example, in hereditary nephritis of Alport's type, associated with mutations in genes encoding ECM proteins, defects in collagen assembly lead to progressive renal failure associated with splitting of the GBM and eventual glomerular and interstitial fibrosis. By contrast in inflammatory renal diseases such as glomerulonephritis, cellular proliferation of components of the glomerulus often precede obvious ultrastructural alteration of the ECM matrix. Cytokines and growth factors implicated in proliferative glomerulonephritis such as interleukin-1, tumor necrosis factor, and transforming growth factor beta can upregulate metalloproteinase expression in renal mesangial cells (Martin J. et al., "Enhancement of glomerular mesangial cell neutral proteinase secretion by macrophages: role of interleukin 1," J. Immunol., 1986; 137:525–529; Marti H. P. et al., "Homology cloning of rat 72 kDa type IV collagenase: Cytokine and second-messenger inducibility in mesangial cells," Biochem. J., 1993;291:441–446; Marti H. P. et al., "Transforming growth factor-b stimulates glomerular mesangial cell synthesis of the 72 kDa type IV collagenase," Am. J. Pathol., 1994; 144:82–94). These metalloprotroteinases are believed to be intimately involved in the aberrant tissue remodeling and cell proliferation characteristic of renal diseases, such as, IgA nephropathy which can progress to through a process of gradual glomerular fibrosis and loss of functional GBM to end-stage renal disease. Metalloproteinase expression has already been well-characterized in experimental immune complex-mediated glomerulonephritis such as the anti-Thy 1.1 rat model (Bagchus W. M., Hoedemaeker P. J., Rozing J., Bakker W. W., "Glomerulonephritis induced by monoclonal anti-Thy 1.1 antibodies: A sequential histological and ultrastructural study in the rat," *Lab. Invest.*, 1986;55:680–687; Lovett D. H., Johnson R. J., Marti H. P., Martin J., Davies M., Couser W. G., "Structural characterization of the mesangial cell type IV collagenase and enhanced expression in a model of immune complex mediated glomerulonephritis," *Am. J. Pathol.*, 1992;141:85–98).

Unfortunately at present, there are very limited therapeutic strategies for modifying the course of progressive renal disease. Although many renal diseases have an inflammatory component, their responses to standard immunosuppressive regimes are unpredictable and potentially hazardous to individual patients. The secondary consequences of gradual nephron failure such as activation of the renin-angiotensin system, accompanied by individual nephron glomerular hyperfiltration and renal hypertension, may be effectively treated with ACE inhibitors or angiotensin II receptor antagonists; but at best, these compounds can only reduce the rate of GFR decline.

A novel strategy to treat at least some renal diseases has been suggested by recent observations of MMP behavior. A rat mesangial cell MMP has been cloned (MMP-2) which is regulated in a tissue specific manner, and in contrast to other cellular sources such as tumor cell lines, is induced by cytokines (Brown P. D., Levy A. T., Margulies I., Liotta L. A., Stetler-Stevenson W. G., "Independent expression and cellular processing of Mr 72,000 type IV collagenase and interstitial collagenase in human tumorigenic cell lines," *Cancer Res.*, 1990;50:6184–6191; Marti H. P. et al., "Homology cloning of rat 72 kDa type IV collagenase: Cytokine and second-messenger inducibility in mesangial cells," *Biochem. J.*, 1993;291:441–446). While MMP-2 can specifically degrade surrounding ECM, it also affects the phenotype of adjacent mesangial cells. Inhibition of MMP-2 by antisense oligonucleotides or transfection techniques can induce a reversion of the proliferative phenotype of cultured mesangial cells to a quiescent or non-proliferative phenotype mimicking the natural in vitro behavior of these cells (Kitamura M. et al., "Gene transfer of metalloproteinase transin induces aberrant behaviour of cultured mesangial cells," *Kidney Int.*, 1994;45: 1580–1586; Turck J. et al., "Matrix metalloproteinase 2 (gelatinase A) regulates glomerular mesangial cell proliferation and differentiation," *J. Biol. Chem.*, 1996;271:15074–15083).

Inhibitors of MMP (MMPi) clearly have potential clinical applications in a host of diseases characterized by disturbance of extracellular matrix-cell interactions resulting in abnormal tissue remodeling (Vincenti M. P. et al., "Using inhibitors of metalloproteinases to treat arthritis," *Arthritis Rheum.*, 1994;8:1115–1126; Grams F. et al., "X-ray structures of human neutrophil collagenase complexed with peptide hydroxyamate and peptide thiol inhibitors. Implications for substrate binding and rational drug design," *Eur. J. Biochem.*, 1995;228:830–841).

Copending U.S. patent applications Ser. No. 60/025,814 filed Sep. 4, 1996, and Serial No. 60/027,138 filed Oct. 2, 1996, disclose a series of biphenyl butyric acids as inhibitors of matrix metalloproteinases.

We have identified a series of benzene butyric acid compounds and their derivatives that are inhibitors of matrix metalloproteinases, particularly collagenase-3, stromelysin-1 and gelatinase A, and thus useful as agents for the treatment of multiple sclerosis, atherosclerotic plaque rupture, restenosis, aortic aneurism, heart failure, left ventricular dilation, periodontal disease, corneal ulceration, treatment of burns, decubital ulcers, wound repair, cancer, inflammation, pain, arthritis, osteoporosis, renal disease, or other autoimmune or inflammatory diseases dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's diseases, prion diseases, myasthenic gravis, and Duchenne's muscular dystrophy.

SUMMARY OF THE INVENTION

Accordingly, a first aspect of the present invention is a compound of Formula I

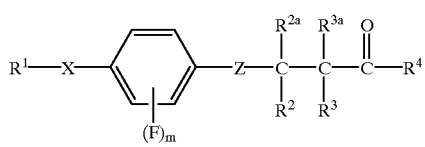

wherein
$R^1$ is hydrogen,
alkyl,
cycloalkyl,
aryl,
arylalkyl,
heteroaryl,
heteroarylalkyl,
heterocycle, or
heterocyclealkyl;
$R^2$, $R^{2a}$, $R^3$, and $R^{3a}$ are either the same or different and are each independently selected from
hydrogen,
fluorine,
—$(C_{1-10}alkyl)_n$—$R^5$ wherein n is zero or an integer of 1, alkyl is unsubstituted or optionally substituted with 1 to 3 substituents selected from
—$OR^7$ wherein $R^7$ is hydrogen or alkyl,
—$SR^7$ wherein $R^7$ is as defined above,
—$CH_2$—S—CO-alkyl,

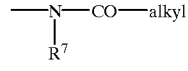

wherein $R^7$ is as defined above,
—CO-alkyl,
—$CO_2$-alkyl,
—O—CO-alkyl,
—S—CO-alkyl,

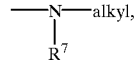

wherein $R^7$ is as defined above,
—SO-alkyl,
—$SO_2$-alkyl,
—CN,

—CF$_3$, or

—HN—SO$_2$-alkyl and,

R$^5$ is hydrogen,
aryl,
heteroaryl,
heterocycle,
N-phthalimide,
N-2,3-naphthylimido,
indol-3-yl,
imidazol-4-yl,
2-, 3-, or 4-pyridyl,
2,4-dioxo-1,5,5-trimethyl-imidazolidin-3-yl or a side chain of a naturally occurring or unnaturally occurring amino acid;

R$^4$ is SH or
OR$^{4a}$ wherein R$^{4a}$ is hydrogen,
alkyl,
arylalkyl,
cycloalkyl,
acyloxymethyl or NHOR$^{4a}$ wherein R$^{4a}$ is as defined above;

X is

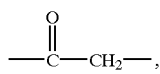

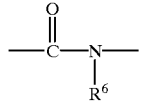

wherein R$^6$ is hydrogen, methyl or optionally R$^1$ and R$^6$ are taken together to form a ring art containing from 4 to 7 carbons which may be unsubstituted or substituted with alkyl,
aryl,
arylalkyl,
heteroaryl,
heteroarylalkyl,
heterocycle, or
heterocyclealkyl,

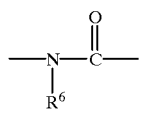

wherein R$^6$ is as defined above,

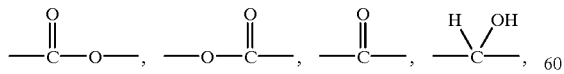

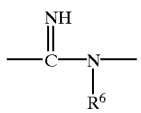

wherein R$^6$ is as defined above,

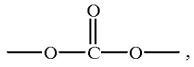

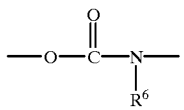

wherein R$^6$ is as defined above,

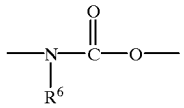

wherein R$^6$ is as defined above,

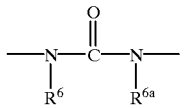

wherein R$^6$ and R$^{6a}$ are either the same or different and are each independently as defined above for R$^6$,

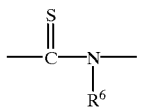

wherein R$^6$ is as defined above,

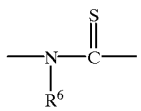

wherein R$^6$ is as defined above,

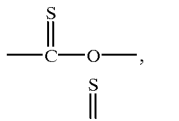

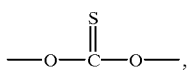

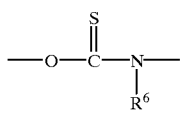

wherein R⁶ is as defined above,

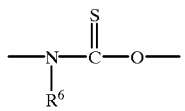

wherein R⁶ is as defined above, or

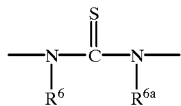

wherein R⁶ and R⁶ᵃ are as defined above;

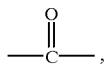,

Z is

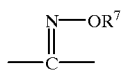

wherein R⁷ is as defined above,

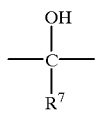

wherein R⁷ is as defined above,

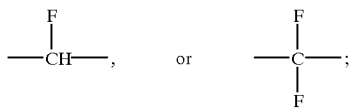;

F is fluorine; and m is zero or an integer of 1 to 4; and corresponding isomers thereof; or a pharmaceutically acceptable salt thereof.

As matrix metalloproteinase inhibitors, the compounds of Formula I are useful as agents for the treatment of multiple sclerosis. They are also useful as agents for the treatment of atherosclerotic plaque rupture, aortic aneurism, heart failure, left ventricular dilation, restenosis, periodontal disease, corneal ulceration, treatment of burns, decubital ulcers, wound repair, cancer metastasis, tumor angiogenesis, inflammation, pain, arthritis, osteoporosis, renal disease, and other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

A still further embodiment of the present invention is a pharmaceutical composition for administering an effective amount of a compound of Formula I in unit dosage form in the treatment methods mentioned above. Finally, the present invention is directed to methods for production of compounds of Formula I.

DETAILED DESCRIPTION OF THE INVENTION

In the compounds of Formula I; the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

"Alkoxy" and "thioalkoxy" are O-alkyl or S-alkyl of from 1 to 6 carbon atoms as defined above for "alkyl".

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, guanidino, amidino, $SO_3H$, CHO,

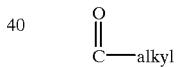

as defined above for alkyl,

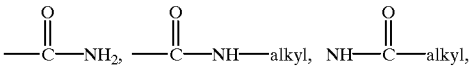

as defined above for alkyl,

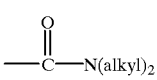

as defined above for alkyl, —$(CH_2)_n2$—$NH_2$ wherein $n^2$ is an integer of 1 to 5, —$(CH_2)_n2$-NH-alkyl as defined above for alkyl and $n^2$, —$(CH_2)_n2$-N(alkyl)₂ as defined above for alkyl and $n^2$,

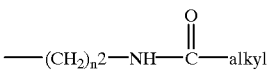

as defined above for alkyl, and $n^2$ and

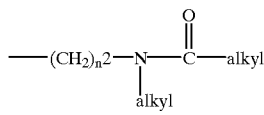

as defined above for alkyl and $n^2$.

The term "arylalkyl" means an aromatic radical attached to an alkyl radical wherein aryl and alkyl are as defined above for example benzyl, phenylethyl, 3-phenylpropyl, (4-chlorophenyl)methyl, and the like.

The term "acyloxymethyl" means a group of the formula

wherein alkyl is as defined above.

The term "heteroaryl" means a 5- and 6-membered heteroaromatic radical containing 1 to 3 heteroatoms selected from N, O, and S and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl, 3-, 4-, or 5-isothiazolyl, 2-, 4-, or 5-imidazolyl, 3-, 4-, or 5-pyrazolyl, or 2- or 5-thiadiazolyl optionally substituted by a substituent selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, guanidino, amidino, $SO_3H$, CHO,

as defined above for alkyl,

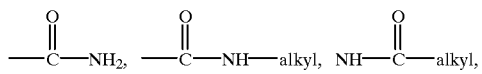

as defined above for alkyl,

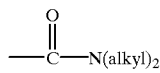

as defined above for alkyl, —$(CH_2)_n2$-$NH_2$ wherein $n^2$ is an integer of 1 to 5, —$(CH_2)_n2$-NH-alkyl as defined above for alkyl and $n^2$, —$(CH_2)_n2$-N(alkyl)$_2$ as defined above for alkyl and $n^2$,

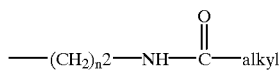

as defined above for alkyl, and $n^2$ and

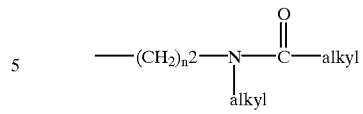

as defined above for alkyl and $n^2$.

The term "heterocycle" means a 3- to 7-membered cycloalkyl radical containing 1 to 3 heteroatoms selected from N, O, and S and includes, for example, 2- and 3-azetidinyl, 3- and 4-azetidinyl-2-one, 4- and 5-imidazolidinyl-2-one, 2,4-dioxo-imidazolidinyl, 2,4-dioxo-1,5,5-trimethyl-imidazolidinyl, 2-, 4-, and 5-thiazolidinyl, 4- and 5-oxazolidinyl-2-one, 2- and 3-tetrahydrofuranyl, 2- and 3-pyrrolidinyl, 2-, 3-, and 4-piperidinyl, 2- and 3-morpholinyl, 2- and 3-piperazinyl, 2-, 3-, and 4-azacycloheptanyl and the like.

The term "heteroarylalkyl" means a heteroaromatic radical attached to an alkyl radical wherein heteroaryl and alkyl are as defined above.

The term "heterocyclealkyl" means a heterocycle radical attached to an alkyl radical wherein heterocycle and alkyl are as defined above.

The term "naturally occurring amino acid" includes alanine, arginine, asparagine, asparatic acid, cysteine, glutamic acid, glutamine, glycine, histidine, leucine, lysine, methionine, phenylalanine, proline, serine, threonine, tryptophan, tyrosine, valine and the like, as well as the D isomers and racemic mixtures thereof.

The term "unnaturally occurring amino acid" includes synthetic amino acids or unusual amino acids not normally found in nature, such as, for example, phenylglycine, 2-pyridylalanine, 2-thienylalanine, cyclohexylalanine octahydroindole-2-carboxylic acid, tetrahydroisoquinoline-3-carboxylic acid, naphythlalanine, and the like.

"Halogen" is fluorine, chlorine, bromine, or iodine.

"Alkali metal" is a metal in Group IA of the periodic table and includes, for example, lithium, sodium, potassium, and the like.

Some of the compounds of Formula I wherein $R^4$ is OH are capable of further forming pharmaceutically acceptable carboxylic esters which are suitable as prodrugs. All of these carboxylic esters are within the scope of the present invention.

Pharmaceutically acceptable carboxylic esters of compounds of Formula I include alkyl, cycloalkyl, arylalkyl, or acyloxymethyl esters.

The alkyl, cycloalkyl, and arylalkyl carboxylic esters of compounds of Formula I can be prepared by methods known to one skilled in the art. For example, the corresponding carboxylic acids can be allowed to react directly with a suitable alcohol in the presence of a suitable acid catalyst to give the carboxylic esters. Alternatively, the carboxylic acids can be allowed to react with one of a number of suitable activating agents, which are known to one skilled in the art, followed by reaction with a suitable alcohol to give the carboxylic esters. Additionally for the 4-hydroxyimino-butyric acids of the present invention, the carboxylic acids can be allowed to cyclo-dehydrate using one of a number of methods known to one skilled in the art to give a cyclic 4,5-dihydro-6-oxo-6H-1,2-oxazine intermediate, which can be allowed to react with a suitable alcohol optionally in the presence of a suitable acid or base catalyst to give the carboxylic esters.

The acyloxymethyl esters of compounds of Formula I can be prepared by methods known to one skilled in the art. For example, the corresponding carboxylic acids can be allowed to react first with a suitable base to give the carboxylate anion, followed by reaction with a carboxylic halomethyl ester, which can be obtained from commercial suppliers or prepared by methods known to one skilled in the art, optionally in the presence of a suitable agent to activate the carboxylic halomethyl ester, which are known to one skilled in the art, to give the acyloxymethyl esters.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *J. of Pharma Sci.,* 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M. et al., "Pharmaceutical Salts," *J. of Pharma Sci.,* 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

In one embodiment of the invention, a preferred compound of Formula I is one wherein X is

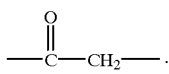

In this embodiment, another preferred compound of Formula I is one wherein X is

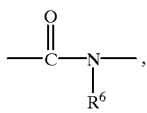

wherein $R^6$ is as defined above.

In this embodiment, another preferred compound of Formula I is one wherein X is

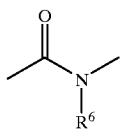

wherein $R^6$ is as defined above; and Z is

In this embodiment, another preferred compound of Formula I is one wherein X is

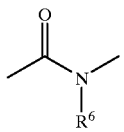

wherein $R^6$ is as defined above; and Z is

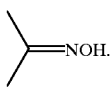

In this embodiment, another preferred compound of Formula I is one wherein X is

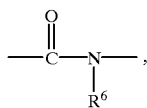

wherein $R^6$ is as defined above;

m is 0; and $R^4$ is OH.

In this embodiment, another preferred compound of Formula I is one wherein X is

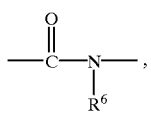

wherein $R^6$ is as defined above;

m is 0; and $R^4$ is NHOH.

In this embodiment, another preferred compound of Formula I is one wherein X is

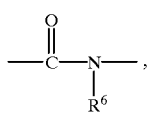

wherein $R^6$ is as defined above;

Z is

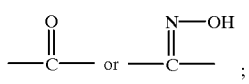

m is 0 or 1;

$R^4$ is OH or NHOH; and $R^6$ is hydrogen.

In this embodiment, another preferred compound of Formula I is one wherein X is

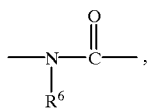

wherein $R^6$ is as defined above.

In this embodiment, another preferred compound of Formula I is one wherein X is

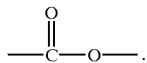

In this embodiment, another preferred compound of Formula I is one wherein X is

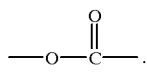

In this embodiment, another preferred compound of Formula I is one wherein X is

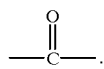

In this embodiment, another preferred compound of Formula I is one wherein X is

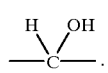

In this embodiment, another preferred compound of Formula I is one wherein X is

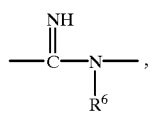

wherein $R^6$ is as defined above.

In this embodiment, another preferred compound of Formula I is one wherein X is

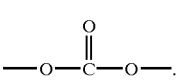

In this embodiment, another preferred compound of Formula I is one wherein X is

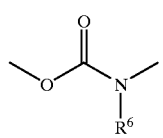

wherein $R^6$ is as defined above.

In this embodiment, another preferred compound of Formula I is one wherein X is

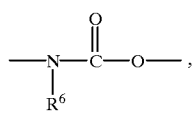

wherein $R^6$ is as defined above.

In this embodiment, another preferred compound of Formula I is one wherein X is

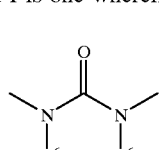

wherein $R^6$ and $R^{6a}$ are as defined above.

In this embodiment, another preferred compound of Formula I is one wherein X is

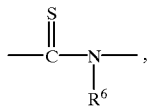

wherein $R^6$ is as defined above.

In this embodiment, another preferred compound of Formula I is one wherein X is

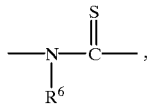

wherein $R^6$ is as defined above.

In this embodiment, another preferred compound of Formula I is one wherein X is

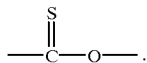

In this embodiment, another preferred compound of Formula I is one wherein X is

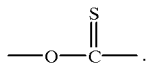

In this embodiment, another preferred compound of Formula I is one wherein X is

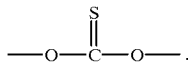

In this embodiment, another preferred compound of Formula I is one wherein X is

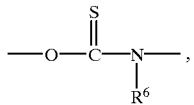

wherein $R^6$ is as defined above.

In this embodiment, another preferred compound of Formula I is one wherein X is

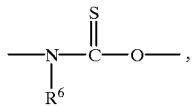

wherein $R^6$ is as defined above.

In this embodiment, another preferred compound of Formula I is one wherein X is

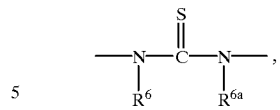

wherein $R^6$ and $R^{6a}$ are as defined above.

In this embodiment, another preferred compound of Formula I is one wherein Z is

In this embodiment, another preferred compound of Formula I is one wherein Z is

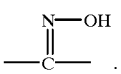

In this embodiment, a more preferred compound of Formula I is one wherein $R^4$ is OH.

In this embodiment, a most preferred compound of Formula I is one wherein $R^4$ is NHOH.

Particularly valuable in this embodiment of the invention is a compound selected from the group consisting of:
4-[4-(4-Bromo-benzoylamino)-phenyl]-4-oxo-butyric acid;
4-(4-Benzoylamino-phenyl)-4-oxo-butyric acid;
4-[4-(4-Chloro-benzoylamino)-phenyl]-4-oxo-butyric acid;
4-[4-(2-Fluoro-benzoylamino)-phenyl]-4-oxo-butyric acid;
4-[4-(3-Fluoro-benzoylamino)-phenyl]-4-oxo-butyric acid;
4-[4-(4-Fluoro-benzoylamino)-phenyl]-4-oxo-butyric acid;
4-[4-(2-Iodo-benzoylamino)-phenyl]-4-oxo-butyric acid;
4-[4-(2,4-Dichloro-benzoylamino)-phenyl]-4-oxo-butyric acid;
4-[4-(2,6-Dichloro-benzoylamino)-phenyl]-4-oxo-butyric acid;
4-[4-(3,4-Dichloro-benzoylamino)-phenyl]-4-oxo-butyric acid;
4-[4-(2,4-Difluoro-benzoylamino)-phenyl]-4-oxo-butyric acid;
4-[4-(4-(4-Bromo-phenyl)-butyrylamino)-phenyl]-4-oxo-butyric acid;
4-[4-(4-(4-Bromo-phenyl)-acetylamino)-phenyl]-4-oxo-butyric acid;
4-[4-(3-Cyano-benzoylamino)-phenyl]-4-oxo-butyric acid;
4-[4-(Benzo[1,3]dioxol-5-yl-carbonylamino)-phenyl]-4-oxo-butyric acid;
4-[4-(Biphenyl-4-yl-carbonylamino)-phenyl]-4-oxo-butyric acid;
4-[4-(4-Cyano-benzoylamino)-phenyl]-4-oxo-butyric acid;
4-[4-(2-Methoxy-benzoylamino)-phenyl]-4-oxo-butyric acid;
4-[4-(3-Methoxy-benzoylamino)-phenyl]-4-oxo-butyric acid;
4-[4-(4-Methoxy-benzoylamino)-phenyl]-4-oxo-butyric acid;
4-[4-(2,4-Dimethoxy-benzoylamino)-phenyl]-4-oxo-butyric acid;
4-[4-(2,5-Dimethoxy-benzoylamino)-phenyl]-4-oxo-butyric acid;
4-[4-(2,6-Dimethoxy-benzoylamino)-phenyl]-4-oxo-butyric acid;
4-[4-(3,5-Dimethoxy-benzoylamino)-phenyl]-4-oxo-butyric acid;

4-Oxo-4-[4-(3,4,5-trimethoxy-benzoylamino)-phenyl]-butyric acid;
4-[4-(4-Methyl-benzoylamino)-phenyl]-4-oxo-butyric acid;
4-[4-(4-Decyl-benzoylamino)-phenyl]-4-oxo-butyric acid;
4-[4-(4-Ethyl-benzoylamino)-phenyl]-4-oxo-butyric acid;
4-[4-(4-Tert-Butyl-benzoylamino)-phenyl]-4-oxo-butyric acid;
4-[4-(4-Butoxy-benzoylamino)-phenyl]-4-oxo-butyric acid;
4-[4-(Cyclohexanecarbonyl-amino)-phenyl]-4-oxo-butyric acid;
4-[4-(Furan-2-yl-carbonyl-amino)-phenyl]-4-oxo-butyric acid;
4-Oxo-4-[4-(thiophen-2-yl-carbonyl-amino)-phenyl]-butyric acid;
4-[4-(3-Chlorobenzo[B]thiophen-2-yl-carbonyl-amino)-phenyl]-4-oxo-butyric acid;
4-Oxo-4-[4-(phenylacetyl-amino)-phenyl]-butyric acid;
4-Oxo-4-[4-(3-phenyl-propionyl-amino)-phenyl]-butyric acid;
4-[-4-(Dodecanoyl-amino)-phenyl]-4-oxo-butyric acid;
4-[-4-(Heptanoyl-amino)-phenyl]-4-oxo-butyric acid;
4-[4-(3-Carboxy-propionyl-amino)-phenyl]-4-oxo-butyric acid;
4-[4-(4-Carboxy-butyryl-amino)-phenyl]-4-oxo-butyric acid;
4-[4-(Carboxy-acetyl-amino)-phenyl]-4-oxo-butyric acid;
4-[4-(3-Nitro-benzoylamino)-phenyl]-4-oxo-butyric acid;
4-[4-(4-Nitro-benzoylamino)-phenyl]-4-oxo-butyric acid;
4-[4-(Butyryl-amino)-phenyl]-4-oxo-butyric acid;
4-[-4-(Decanoyl-amino)-phenyl]-4-oxo-butyric acid;
4-[4-(4-Chloro-phenoxy-acetylamino)-phenyl]-4-oxo-butyric acid;
4-[4-(3,4-Dimethoxy-benzoylamino)-phenyl]-4-oxo-butyric acid;
4-[4-(3,4-Dimethoxy-phenylacetyl-amino)-phenyl]-4-oxo-butyric acid;
4-[4-(Napthyl-2-yl-carbonylamino)-phenyl]-4-oxo-butyric acid;
4-Oxo-4-[4-(pyridin-3-yl-carbonylamino)-phenyl]-butyric acid;
4-[4-(Adamantan-1-yl-carbonylamino)-phenyl]-4-oxo-butyric acid;
4-[4-(Oleoyl-amino)-phenyl]-4-oxo-butyric acid;
4-[4-(Nonanoyl-amino)-phenyl]-4-oxo-butyric acid;
4-Oxo-4-[4-(propionylamino)-phenyl]-butyric acid;
4-[4-(2-Acetoxy-2,2-dimethyl-acetylamino)-phenyl]-4-oxo-butyric acid;
4-Oxo-4-[4-(phenoxy-acetylamino)-phenyl]-butyric acid;
4-[4-(Oxalamino)-phenyl]-4-oxo-butyric acid;
4-[4-(4-Chloro-3-nitro-benzoylamino)-phenyl]-4-oxo-butyric acid;
4-Oxo-4-[4-(phenylazo-benzoylamino)-phenyl]-butyric acid;
4-[4-(Cinnamoylamino)-phenyl]-4-oxo-butyric acid;
(±)-2-(Acetylthio)methyl-4-[4-(4-methyl-benzoylamino)-phenyl]-4-oxo-butyric acid;
(±)-3-(Acetylthio)methyl-4-[4-(4-methyl-benzoylamino)-phenyl]-4-oxo-butyric acid;
(±)-2-(2,4-Dioxo-1,5,5-trimethyl-imidazolidin-3-yl)methyl-4-[4-(4-methyl-benzoylamino)-phenyl]-4-oxo-butyric acid;
(±)-2-(4-Benzyloxy-phenyl)methyl-4-[4-(4-methyl-benzoylamino)-phenyl]-4-oxo-butyric acid;
(±)-4-[4-(4-Methyl-benzoylamino)-phenyl]-4-oxo-2-(3-phenyl-propyl)-butyric acid;
(±)-4-[4-(4-Methyl-benzoylamino)-phenyl]-4-oxo-2-(2-phthalimindo-ethyl)-butyric acid;
(±)-2-(4-Methyl-benzenesulfonyl)amino-4-[4-(4-methyl-benzoylamino)-phenyl]-4-oxo-butyric acid;
(±)-4-[4-(4-Methyl-benzoylamino)-phenyl]-4-oxo-3-(pyridin-3-yl)methyl-butyric acid;
4-[4-(Octanoylamino)-phenyl]-4-oxo-butyric acid;
4-[4-(4-Heptyl-benzoylamino)-phenyl]-4-oxo-butyric acid;
4-[4-(2-Naphthoylamino)-phenyl]-4-oxo-butyric acid;
4-Oxo-4-[4-(4-trifluoromethyl-benzoylamino)-phenyl]-butyric acid;
4-Oxo-4-[4-(2,3,4,5,6-pentafluoro-benzoylamino)-phenyl]-butyric acid;
4-[4-(2-Fluoro-4-trifluoromethyl-benzoylamino)-phenyl]-4-oxo-butyric acid;
4-[4-(3-Fluoro-4-trifluoromethyl-benzoylamino)-phenyl]-4-oxo-butyric acid;
4-[4-(4-Hexyloxy-benzoylamino)-phenyl]-4-oxo-butyric acid;
4-[4-(2-Benzo[b]thiophene-carbonylamino)-phenyl]-4-oxo-butyric acid;
4-Oxo-4-[4-(2-quinoxaloylamino)-phenyl-butyric acid;
4-[4-(4-Dipropylaminosulfonyl-benzoylamino)-phenyl]-4-oxo-butyric acid;
4-Oxo-[4-(3-phenyl-ureido)-phenyl]-butyric acid;
{4-[3-(4-Chloro-phenyl)-ureido]-phenyl}-4-oxo-butyric acid;
{4-[3-(4-Bromo-phenyl)-ureido]-phenyl}-4-oxo-butyric acid;
{4-[3-(4-Fluoro-phenyl)-ureido]-phenyl}-4-oxo-butyric acid;
4-Oxo-{4-[3-(4-trifluoro-phenyl)-ureido]-phenyl}-butyric acid;
{4-[3-(4-Methoxy-phenyl)-ureido]-phenyl}-4-oxo-butyric acid;
{4-[3-(4-Methyl-phenyl)-ureido]-phenyl}-4-oxo-butyric acid;
4-Oxo-{4-[3-(thiophen-2-yl)-ureido]-phenyl}-butyric acid;
4-Oxo-4-[4-(phenoxycarbonylamino)-phenyl]-butyric acid;
4-{4-[(4-Chloro-phenoxy)-carbonylamino]-phenyl}-4-oxo-butyric acid;
4-{4-[(4-Bromo-phenoxy)-carbonylamino]-phenyl}-4-oxo-butyric acid;
4-{4-[(4-Fluoro-phenoxy)-carbonylamino]-phenyl}-4-oxo-butyric acid;
4-{4-[(4-Methoxy-phenoxy)-carbonylamino]-phenyl}-4-oxo-butyric acid;
4-{4-[(4-Methyl-phenoxy)-carbonylamino]-phenyl}-4-oxo-butyric acid;
4-Oxo-4-{4-[(4-trifluoromethyl-phenoxy)-carbonylamino]-phenyl}-butyric acid;
4-Oxo-{4-[4-(2-thiophenoxy)-carbonylamino]-phenyl}-butyric acid;
4-[4-(4-Bromo-benzoylamino)-phenyl]-4-hydroxyimino-butyric acid;
4-(4-Benzoylamino-phenyl)-4-hydroxyimino-butyric acid;
4-[4-(4-Chloro-benzoylamino)-phenyl]-4-hydroxyimino-butyric acid;
4-[4-(2-Fluoro-benzoylamino)-phenyl]-4-hydroxyimino-butyric acid;
4-[4-(3-Fluoro-benzoylamino)-phenyl]-4-hydroxyimino-butyric acid;
4-[4-(4-Fluoro-benzoylamino)-phenyl]-4-hydroxyimino-butyric acid;
4-Hydroxyimino-4-[4-(2-iodo-benzoylamino)-phenyl]-butyric acid;
4-[4-(2,4-Dichloro-benzoylamino)-phenyl]-4-hydroxyimino-butyric acid;
4-[4-(2,6-Dichloro-benzoylamino)-phenyl]-4-hydroxyimino-butyric acid;

4-[4-(3,4-Dichloro-benzoylamino)-phenyl]-4-hydroxyimino-butyric acid;
4-[4-(2,4-Difluoro-benzoylamino)-phenyl]-4-hydroxyimino-butyric acid;
4-[4-(4-(4-Bromo-phenyl)-butyrylamino)-phenyl]-4-hydroxyimino-butyric acid;
4-[4-(4-4-Bromo-phenyl)-acetylamino)-phenyl]-4-hydroxyimino-butyric acid;
4-[4-(3-Cyano-benzoylamino)-phenyl]-4-hydroxyimino-butyric acid;
4-[4-(Benzo[1,3]dioxol-5-yl-carbonylamino)-phenyl]-4-hydroxyimino-butyric acid;
4-[4-(Biphenyl-4-yl-carbonylamino)-phenyl]-4-hydroxyimino-butyric acid;
4-[4-(4-Cyano-benzoylamino)-phenyl]-4-hydroxyimino-butyric acid;
4-Hydroxyimino-4-[4-(2-methoxy-benzoylamino)-phenyl]-butyric acid;
4-Hydroxyimino-4-[4-(3-methoxy-benzoylamino)-phenyl]-butyric acid;
4-Hydroxyimino-4-[4-(4-methoxy-benzoylamino)-phenyl]-butyric acid;
4-[4-(2,4-Dimethoxy-benzoylamino)-phenyl]-4-hydroxyimino-butyric acid;
4-[4-(2,5-Dimethoxy-benzoylamino)-phenyl]-4-hydroxyimino-butyric acid;
4-[4-(2,6-Dimethoxy-benzoylamino)-phenyl]-4-hydroxyimino-butyric acid;
4-[4-(3,5-Dimethoxy-benzoylamino)-phenyl]-4-hydroxyimino-butyric acid;
4-Hydroxyimino-4-[4-(3,4,5-trimethoxy-benzoylamino)-phenyl]-butyric acid;
4-Hydroxyimino-4-[4-(4-Methyl-benzoylamino)-phenyl]-butyric acid;
4-[4-(4-Decyl-benzoylamino)-phenyl]-4-hydroxyimino-butyric acid;
4-[4-(4-Ethyl-benzoylamino)-phenyl]-4-hydroxyimino-butyric acid;
4-[4-(4-Tert-Butyl-benzoylamino)-phenyl]-4-hydroxyimino-butyric acid;
4-[4-(4-Butoxy-benzoylamino)-phenyl]-4-hydroxyimino-butyric acid;
4-[4-(Cyclohexanecarbonyl-amino)-phenyl]-4-hydroxyimino-butyric acid;
4-[4-(Furan-2-yl-carbonyl-amino)-phenyl]-4-hydroxyimino-butyric acid;
4-Hydroxyimino-4-[4-(thiophen-2-yl-carbonyl-amino)-phenyl]-butyric acid;
4-[4-(3-Chlorobenzo[B]thiophen-2-yl-carbonyl-amino)-phenyl]-4-hydroxyimino-butyric acid;
4-Hydroxyimino-4-[4-(phenylacetyl-amino)-phenyl]-butyric acid;
4-Hydroxyimino-4-[4-(3-phenyl-propionyl-amino)-phenyl]-butyric acid;
4-[4-(2,2-Dimethyl-pentanoyl-amino)-phenyl]-4-hydroxyimino-butyric acid;
4-[-4-(Dodecanoyl-amino)-phenyl]-4-hydroxyimino-butyric acid;
4-[-4-(Heptanoyl-amino)-phenyl]-4-hydroxyimino-butyric acid;
4-[4-(3-Carboxy-propionyl-amino)-phenyl]-4-hydroxyimino-butyric acid;
4-[4-(4-Carboxy-butyryl-amino)-phenyl]-4-hydroxyimino-butyric acid;
4-[4-(Carboxy-acetyl-amino)-phenyl]-4-hydroxyimino-butyric acid;
4-Hydroxyimino-4-[4-(3-nitro-benzoylamino)-phenyl]-butyric acid;
4-Hydroxyimino-4-[4-(4-nitro-benzoylamino)-phenyl]-butyric acid;
4-[4-(Butyryl-amino)-phenyl]-4-hydroxyimino-butyric acid;
4-[-4-(Decanoyl-amino)-phenyl]-4-hydroxyimino-butyric acid;
4-[4-(Diphenylacetyl-amino)-phenyl]-4-hydroxyimino-butyric acid;
4-[4-(4-Chloro-phenoxy-acetylamino)-phenyl]-4-hydroxyimino-butyric acid;
4-[4-(3,4-Dimethoxy-benzoylamino)-phenyl]-4-hydroxyimino-butyric acid;
4-[4-(3,4-Dimethoxy-phenylacetyl-amino)-phenyl]-4-hydroxyimino-butyric acid;
4-Hydroxyimino-4-[4-(napthyl-2-yl-carbonylamino)-phenyl]-butyric acid;
4-Hydroxyimino-4-[4-(pyridin-3-yl-carbonylamino)-phenyl]-butyric acid;
4-[4-(Adamantan-1-yl-carbonylamino)-phenyl]-4-hydroxyimino-butyric acid;
4-Hydroxyimino-4-[4-(oleoyl-amino)-phenyl]-butyric acid;
4-Hydroxyimino-4-[4-(nonanoyl-amino)-phenyl]-butyric acid;
4-Hydroxyimino-4-[4-(propionylamino)-phenyl]-butyric acid;
4-[4-(2-Acetoxy-2,2-dimethyl-acetylamino)-phenyl]-4-hydroxyimino-butyric acid;
4-Hydroxyimino-4-[4-(2-phenoxy-propionylamino)-phenyl]-butyric acid;
4-Hydroxyimino-4-[4-(phenoxy-acetylamino)-phenyl]-butyric acid;
4-Hydroxyimino-4-[4-(oxalamino)-phenyl]-butyric acid;
4-[4-(4-Chloro-3-nitro-benzoylamino)-phenyl]-4-hydroxyimino-butyric acid;
4-Hydroxyimino-4-[4-(phenylazo-benzoylamino)-phenyl]-butyric acid;
4-[4-(Cinnamoylamino)-phenyl]-4-hydroxyimino-butyric acid;
(±)-2-(Acetylthio)methyl-4-hydroxyimino-4-[4-(4-methyl-benzoylamino)-phenyl]-butyric acid;
(±)-3-(Acetylthio)methyl-4-hydroxyimino-4-[4-(4-methyl-benzoylamino)-phenyl]-butyric acid;
(±)-2-(2,4-Dioxo-1,5,5-trimethyl-imidazolidin-3-yl)methyl-4-hydroxyimino-4-[4-(4-methyl-benzoylamino)-phenyl]-butyric acid;
(±)-2-(4-Benzyloxy-phenyl)methyl-4-hydroxyimino-4-[4-(4-methyl-benzoylamino)-phenyl]-butyric acid;
(±)-4-Hydroxyimino-4-[4-(4-methyl-benzoylamino)-phenyl]-2-(3-phenyl-propyl)-butyric acid;
(±)-4-Hydroxyimino-4-[4-(4-methyl-benzoylamino)-phenyl]-2-(2-phthalimindo-ethyl)-butyric acid;
(±)-4-Hydroxyimino-2-(4-methyl-benzenesulfonyl)amino-4-[4-(4-methyl-benzoylamino)-phenyl]-butyric acid; and
(±)-4-Hydroxyimino-4-[4-(4-methyl-benzoylamino)-phenyl]-3-(pyridin-3-yl)methyl-butyric acid;
and corresponding isomers thereof; or a pharmaceutically acceptable salt thereof.

The compounds of Formula I are valuable inhibitors of gelatinase A and/or stromelysin-1 and/or collagenase-3 (MMP-13). It has been shown previously that inhibitors of matrix metalloproteinases have efficacy in models of disease states like arthritis and metastasis that depend on modification of the extracellular matrix.

In vitro experiments were carried out which demonstrate the efficacy of compounds of Formula I as potent and specific inhibitors of gelatinase A, collagenase-3, and stromelysin-1. Experiments were carried out with the catalytic domains of the proteinases. Table 1 shows the activity of Examples 1–36 versus MMP-2CD (gelatinase A catalytic domain), MMP-3CD (stromelysin-1 catalytic domain), and MMP-13CD (collagenase-3 catalytic domain). $IC_{50}$ values were determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli*," *Biochemistry*, 1992;31:11231–11235; Ye Q.-Z., Johnson L. L., Yu A. E., and Hupe D., "Reconstructed 19 kDa catalytic domain of gelatinase A is an active proteinase," *Biochemistry*, 1995;34:4702–4708.) MMP-13CD was expressed from a synthetic gene and purified from *Escherichia coli* cell culture according to a previously described method (Ye Q.-Z., Johnson L. L., and Baragi V., "Gene synthesis and expression in *E. coli* for PUMP, a human matrix metalloproteinase," *Biochemical and Biophysical Research Communications*, 1992;186:143–149.)

TABLE 1

| Example[a] | $IC_{50}$ ($\mu$M) | | |
|---|---|---|---|
| | MMP-2CD | MMP-3CD | MMP-13CD |
| 1 | 0.22 | 1.55 | 5.8 |
| 2 | 0.41 | 1.1 | 3.8 |
| 3 | 9.5 | 8.15 | 100 |
| 4 | 1.9 | 6.2 | 100 |
| 5 | 1.9 | 9.8 | 100 |
| 6 | 1.7 | 2.8 | 85 |
| 7 | 100 | 20 | 100 |
| 8 | 15 | 3 | 0 |
| 9 | 85 | 75 | 3 |
| 10 | 79 | 66 | 8 |
| 11 | 46 | 21 | 9 |
| 12 | 75 | 31 | 11 |
| 13 | 26 | 11 | 0 |
| 14 | 26 | 48 | 7 |
| 15 | 83 | 70 | 11 |
| 16 | 97 | 85 | 60 |
| 17 | 97 | 78 | 65 |
| 18 | 82 | 38 | 16 |
| 19 | 86 | 72 | 9 |
| 20 | 93 | 81 | 30 |
| 21 | 78 | 23 | 8 |
| 22 | 62 | 35 | 0 |
| 23 | 54 | 39 | 0 |
| 24 | 15 | 4 | 0 |
| 25 | 18 | 13 | 0 |
| 26 | 0.12 | 0.82 | 24 |
| 27 | 0.07 | 0.34 | 9.8 |
| 28 | 0.11 | 0.55 | 17 |
| 29 | 0.46 | 2.4 | 40 |
| 30 | 0.93 | 5 | 100 |
| 31 | 0.13 | 1.7 | 19 |
| 32 | 0.91 | 19 | 100 |
| 33 | 52 | 24 | 100 |
| 34 | 100 | 6.6 | 100 |
| 35 | 38 | 13 | 100 |
| 36 | 41 | 17 | 100 |

[a]Data for Examples 8 through 25, inclusive, are % inhibition of the enzyme at 10 $\mu$M concentration of inhibitor.

The following list contains abbreviations and acronyms used within the schemes and text:

| GBM | Glomerular basement membrane |
|---|---|
| ECM | Extracellular matrix |
| Bu | Normal butyl |
| n-Bu | Normal butyl |
| CNS | Central nervous system |

-continued

| $CH_2Cl_2$ | Dichloromethane |
|---|---|
| EAE | Experimental autoimmune encephalomyelitis |
| MMP | Matrix metalloproteinase |
| TIMPs | Tissue inhibitors of matrix metalloproteinases |
| VSMC | Vascular smooth muscle cell |
| TFA | Trifluoroacetic acid |
| $ClSnBu_3$ | Tributyltin chloride |
| $IC_{50}$ | Concentration of compound required to inhibit 50% of enzyme activity |
| HCl | Hydrogen chloride |
| KHMDS | Potassium hexamethyldisilazide |
| n-BuLi | n-butyl lithium |
| $(Bu_3Sn)$ | Hexabutylditin |
| $MnCl_2$ | Manganese chloride |
| THF | Tetrahydrofuran |
| Pd | Palladium |
| $H_2S$ | Hydrogen sulfide |
| NaH | Sodium hydride |
| LiOH | Lithium hydroxide |
| $H_2O_2$ | Hydrogen peroxide |
| $H_2O$ | Water |
| CDI | 1,1'-Carbonyldiimidazole |
| NBS | N-Bromosuccinimide |
| $CCl_4$ | Carbon tetrachloride |
| hv | light |
| HBr | Hydrogen bromide |
| KBr | Potassium bromide |
| $NaNO_2$ | Sodium nitrite |
| Me | Methyl |
| Et | Ethyl |
| t-Bu | tertiary butyl |
| Bn | Benzyl |
| BOC | tertiary butoxycarbonyl |
| CBZ | Benzyloxycarbonyl |
| FMOC | 9-Fluorenylmethoxycarbonyl |
| $(COCl)_2$ | Oxalyl chloride |
| NFSI | N-Fluorodibenzenesulfonamide |
| $Et_3SiH$ | Triethylsilane |
| LDA | Lithium diisopropylamide |
| EtOH | Ethanol |
| MeOH | Methanol |
| $NaBH_4$ | Sodium borohydride |
| DAST | Diethylamino sulfur trifluoride |
| TMS-Cl | Chlorotrimethylsilane |
| DMF | Dimethylformamide |
| KOH | Potassium hydroxide |
| NaOH | Sodium hydroxide |
| p-TsOH | para-Toluenesulfonic acid |
| halo | Chlorine, bromine, iodine, or fluorine |
| $CHCL_3$ | Chloroform |
| E | Entgegen |
| Z | Zusammen |
| Mg | Magnesium metal |
| $H_2NOH$ | Hydroxylamine |
| $H_2NOH \cdot HCl$ | Hydroxylamine hydrochloride |
| $NaHCO_3$ | Sodium bicarbonate |
| $Na_2CO_3$ | Sodium carbonate |
| $K_2CO_3$ | Potassium carbonate |
| TEA | Triethylamine |
| $B(OiPr)_3$ | Triisopropylborate |
| $BF_3 \cdot Et_2O$ | Boron trifluoride etherate |
| Ph | Phenyl |
| $CDCl_3$ | Deuterated chloroform |
| DMSO-$d_6$ | Deuterated dimethylsulfoxide |
| $MgSO_4$ | Magnesium sulfate |
| $Na_2SO_4$ | Sodium sulfate |
| $ZnCl_2$ | Zinc chloride |
| $VCl_3$ | Vanadium chloride |
| $FeCl_3$ | Ferric chloride |
| $Pd(Ph_3)_4$ | Palladium tetrakis(triphenylphosphine) |
| $Fe(acac)_3$ | Iron(III)acetylacetonate |
| $PdCl_2(PPh_3)_2$ | Bis(triphenylphosphine)palladium(II)chloride |
| $H^1$-NMR | Proton nuclear magnetic resonance spectrum |
| PPM | Parts per million |
| MS | Mass spectrum |
| DMAP | 4-Dimethylaminopyridine |

Compounds of formulas (6), (10), (13), and (15) can be prepared according to the route as set forth in Scheme 1.

In Scheme 1, a compound of formula (1) wherein $R^8$ is defined as shown in Scheme 1, obtained from commercial sources or prepared according to methods known to one skilled in the art, can be allowed to react with a compound of formula (2) under Friedel-Crafts acylation conditions to give a compound of formula (3). Alternatively, a compound of formula (3) can be prepared by reaction of a compound of formula (4), obtained from commercial sources or prepared according to methods known to one skilled in the art, with hexabutylditin in the presence of a suitable catalyst such as, for example, palladium tetrakis (triphenylphosphine) and the like in a suitable solvent such as, for example, toluene, benzene, and the like at temperatures from about 0° C. to about 150° C., or by reaction of a compound of formula (4) with an organolithium such as, for example, n-butyl lithium or magnesium metal in a suitable solvent such as, for example, tetrahydrofuran, diethyl ether, and the like at temperatures from about −80° C. to about 65° C., followed by reaction with tributyltin chloride, and the tin intermediate so formed can be allowed to react with a compound of formula (2) in the presence of a suitable catalyst such as, for example, bis(triphenylphosphine) palladium(II)chloride, and the like at temperatures from about −80° C. to about 150° C. Alternatively, a compound of formula (3) can be prepared by reaction of a compound of formula (4) with a suitable metallating reagent such as, for example, n-butyl lithium or magnesium metal in a suitable solvent such as, for example, tetrahydrofuran, tert-butylmethyl ether, and the like at temperatures from about −80° C. to about 65° C., followed by reaction of the resulting intermediate with manganese chloride in the presence of iron(III)acetylacetonate and hexane, followed by reaction of the second intermediate with a compound of formula (2). A compound of formula (3) can be allowed to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction of the resulting enolate with a compound of formula (5) at temperatures from about −100° C. to about 65° C., and the resulting product can be selectively deprotected to give a compound of formula (6) wherein $R^{8a}$ is defined as shown in Scheme 1.

Alternatively, a compound of formula (3) can be allowed to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction of the resulting enolate with a compound of formula (7) or NFSI for $R^{2a}$ equals fluorine at temperatures from about −100° C. to about 65° C. to give a compound of formula (8). A compound of formula (8) can be allowed to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction of the resulting enolate with a compound of formula (5) at temperatures from about −100° C. to about 65° C. to give a compound of formula (9). A compound of formula (9) can be selectively deprotected to give a compound of formula (10).

Alternatively, a compound of formula (9) can be allowed to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction of the resulting enolate with a compound of formula (11) at temperatures from about −100° C. to about 65° C. to give a compound of formula (12). A compound of formula (12) can be selectively deprotected to give a compound of formula (13).

Alternatively, a compound of formula (12) can be allowed to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction of the resulting enolate with a compound of formula (14) or NFSI for $R^{3a}$ equals fluorine at temperatures from about −100° C. to about 65° C., and the product can be selectively deprotected to give a compound of formula (15).

Compounds of formulas (15), (18), (22), and (25) can be prepared according to the route as set forth in Scheme 2.

In Scheme 2, a compound of formula (1), obtained from commercial sources or prepared according to methods known to one skilled in the art, can be allowed to react with bromoacetyl chloride under Friedel-Crafts acylation conditions to give a compound of formula (16). Alternatively, a compound of formula (16) can be prepared by reaction of a compound of formula (4), obtained from commercial sources or prepared according to methods known to one skilled in the art, with hexabutylditin in the presence of a suitable catalyst such as, for example, palladium tetrakis (triphenylphosphine) and the like in a suitable solvent such as, for example, toluene, benzene, and the like at temperatures from about 0° C. to about 150° C., or by reaction of a compound of formula (4) with an organolithium such as, for example, n-butyl lithium or magnesium metal in a suitable solvent such as, for example, tetrahydrofuran, diethyl ether, and the like at temperatures from about −80° C. to about 65° C., followed by reaction with tributyltin chloride, and the tin intermediate so formed can be allowed to react with bromoacetyl chloride in the presence of a suitable catalyst such as, for example, bis(triphenylphosphine)palladium(II) chloride, and the like at temperatures from about −80° C. to about 150° C. Alternatively, a compound of formula (16) can be prepared by reaction of a compound of formula (4), with a suitable metallating reagent such as, for example, n-butyl lithium or magnesium metal in a suitable solvent such as, for example, tetrahydrofuran, tert-butylmethyl ether, and the like at temperatures from about −80° C. to about 65° C., followed by reaction of the resulting intermediate with manganese chloride in the presence of iron(III) acetylacetonate and hexane, followed by reaction of the second intermediate with bromoacetyl chloride.

A compound of formula (16) can be allowed to react with an enolate derived from deprotonation of a compound of formula (20), prepared by allowing a compound of formula (17) to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction with a compound of formula (14) or NFSI for $R^{3a}$ equals fluorine at temperatures from about −100° C. to about 65° C., using a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C. to give a compound of formula (21). Alternatively, a compound of formula (17) can be allowed to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction with a compound of formula (16) to give a compound of formula (18). A compound of formula (18) can be selectively deprotected to give a compound of formula (19).

A compound of formula (21) can be selectively deprotected to give a compound of formula (22).

Alternatively, a compound of formula (21) can be allowed to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction of the resulting enolate with a compound of formula (23) to give a compound of formula (24). A compound of formula (24) can be selectively deprotected to give a compound of formula (25).

Alternatively, a compound of formula (24) can be allowed to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction of the resulting enolate with a compound of formula (7) or NFSI for $R^{2a}$ equals fluorine to give a compound of formula (15).

Compounds of formula (32) wherein $R^{2a}$ and $R^{3a}$ are hydrogen can be prepared as set forth in Scheme 3.

In Scheme 3, a suitable chiral 4-substituted-2-oxazolidinone such as, for example, (R)-4-benzyl-2-oxazolidinone or (S)-4-benzyl-2-oxazolidinone and the like can be allowed to react with a compound of formula (2a) in the presence of a suitable coupling agent such as, for example, 1,1'-carbonyldiimidazole, N,N'-dicyclohexylcarbodiimide, and the like in a suitable solvent such as, for example, tetrahydrofuran, dichloromethane, and the like at temperatures from about −80° C. to about 65° C. to give a compound of formula (26). Alternatively, a compound of formula (26) can be prepared by reacting a suitable chiral 4-substituted-2-oxazolidinone such as, for example, (R)-4-benzyl-2-oxazolidinone or (S)-4-benzyl-2-oxazolidinone and the like with a suitable base such as, for example, sodium hydride, lithium diisopropylamide, and the like in a suitable solvent such as, for example, tetrahydrofuran, diethyl ether, and the like at temperatures from about −80° C. to about 65° C. followed by reaction of the resulting anion with a compound of formula (2). A compound of formula (26) can be allowed to react with a suitable base such as, for example, lithium diisopropylamide, potassium hexamethyldisilazide, sodium hydride, and the like in a suitable solvent such as, for example, tetrahydrofuran, diethyl ether, and the like at temperatures from about −100° C. to about 65° C., followed by reaction of the resulting enolate with a compound of formula (27), prepared in racemic form by reaction of a compound of formula (28) with N-bromosuccinimide (NBS) in a suitable solvent such as, for example, carbon tetrachloride, heptane, and the like in the presence of a suitable catalyst such as, for example, light and/or heat and/or a peroxide such as, for example, benzoyl peroxide, or prepared in chiral form by reaction of a compound of formula (29) with aqueous hydrogen bromide, sodium nitrite, and potassium bromide, and the resulting intermediate can be reacted with a compound of formula (30) in the presence of a coupling agent such as, for example, 1,1'-carbonyldiimidazole, N,N'-dicyclohexylcarbodiimide, and the like in a suitable solvent such as, for example, tetrahydrofuran, dichloromethane, and the like at temperatures from about −80° C. to about 65° C., to give a compound of formula (31). A compound of formula (31) can be separated into its diastereomers by methods known to one skilled in the art, and the resulting individual isomers can be selectively deprotected using suitable conditions such as, for example, lithium hydroxide and hydrogen peroxide in a suitable solvent system such as, for example, tetrahydrofuran-water followed by reaction of the resulting carboxylic acid with a suitable chlorinating reagent such as, for example, oxalyl chloride and the like to give a compound of formula (32). A compound of formula (32) can be allowed to react with a compound of formula (1) under Friedel-Crafts acylation conditions or with a compound of formula (4) using conditions as described in Scheme 1 for the reaction of a compound of formula (4) with a compound of formula (2), and the product can be selectively deprotected to give a compound of formula (33).

Compounds of formulas (36), (37), (39), (40), (44), and (45) wherein X is —CO—NR$^6$, —O—CO—NR$^6$, —N(R$^{6a}$)—CO—NR$^6$, —CS—NR$^6$, —O—CS—NR$^6$, or —N(R$^{6a}$)—CS—NR$^6$ can be prepared as set forth in Scheme 4.

In Scheme 4, compounds of formulas (6), (10), (13), (15), (19), (22), (25), and (33) wherein $R^{8a}$ equals HN(R$^6$) can be allowed to react with a compound of formula (34) in the presence of a suitable base such as, for example, triethylamine, ethyldiisopropylamine, and the like in a suitable solvent such as, for example, dichloromethane, diethyl ether, tetrahydrofuran, and the like at temperatures from about −50° C. to about 65° C. to give a compound of formula (36). Alternatively, a compound of formula (36) can be prepared from a compounds of formulas (6), (10), (13), (15), (19), (22), (25), and (33) by reaction with a compound of formula (35) in the presence of a suitable coupling agent such as, for example, 1,1'-carbonyldiimidazole, N,N'-dicyclohexylcarbodiimide, and the like in a suitable solvent such as, for example, tetrahydrofuran, dichloromethane, and the like at temperatures from about −80° C. to about 65° C. A compound of formula (36) can be allowed to react with a sulfurating reagent such as, for example, P$_4$S$_{10}$ or Lawesson's reagent in a suitable solvent such as, for example, tetrahydrofuran, tert-butylmethyl ether, and the like at temperatures from about −20° C. to about 150° C. to give a compound of formula (37).

Alternatively, compounds of formulas (6), (10), (13), (15), (19), (22), (25), and (33) can be allowed to react with a compound of formula (38) in the presence of a suitable base such as, for example, triethylamine, ethyldiisopropylamine, and the like in a suitable solvent such as, for example, dichloromethane, diethyl ether, tetrahydrofuran, and the like at temperatures from about −50° C. to about 65° C. to give a compound of formula (39). A compound of formula (39) can be allowed to react with a sulfurating reagent such as, for example, P$_4$S$_{10}$ or Lawesson's reagent in a suitable solvent such as, for example, tetrahydrofuran, tert-butylmethyl ether, and the like at temperatures from about −20° C. to about 150° C. to give a compound of formula (40).

Alternatively, compounds of formulas (6), (10), (13), (15), (19), (22), (25), and (33) can be allowed to react with a compound of formula (41) for $R^{6a}$ not equal to hydrogen, prepared by allowing a compound of formula (42) to react with a suitable acylating reagent such as, for example, phosgene, diphosgene, triphosgene, 4-nitrophenyl chloroformate, and the like with or without the presence of a suitable base such as, for example, triethylamine, ethyldiisopropylamine, and the like in a suitable solvent such as, for example, dichloromethane, diethyl ether, tetrahydrofuran, and the like at temperatures from about −50° C. to about 95° C., in the presence of a suitable base such as, for example, triethylamine, ethyldiisopropylamine, and the like in a suitable solvent such as, for example, dichloromethane, diethyl ether, tetrahydrofuran, and the like at temperatures from about −50° C. to about 65° C. to give a compound of formula (44). Alternatively, a compound of formula (44) wherein $R^{6a}$ equals hydrogen can be prepared by allowing the reaction of compounds of formula (6), (10), (13), (15), (19), (22), (25), and (33) with a compound of formula (43) in a suitable solvent such as, for example, dichloromethane, diethyl ether, tetrahydrofuran, and the like with or without the presence of a suitable catalyst such as, for example, 4-dimethylamino-pyridine, tributylphosphine, and the like at temperatures from about −50° C. to about 95° C. A compound of formula (44) can be allowed to react with a sulfurating reagent such as, for example, $P4S_{10}$ or Lawesson's reagent in a suitable solvent such as, for example, tetrahydrofuran, tert-butylmethyl ether, and the like at temperatures from about −20° C. to about 150° C. to give a compound of formula (45).

Compounds of formulas (46), (47), (48), (49), (53), and (54) wherein X is —CO—O, —O—CO—O, —N($R^6$)—CO—O, —CS—O, —O—CS—O, or —N($R^6$)—CS—O can be prepared as set forth in Scheme 5.

In Scheme 5, compounds of formulas (6), (10), (13), (15), (19), (22), (25), and (33) wherein $R^{8a}$ equals HO— can be allowed to react with a compound of formula (34) in the presence of a suitable base such as, for example, triethylamine, ethyldiisopropylamine, and the like in a suitable solvent such as, for example, dichloromethane, diethyl ether, tetrahydrofuran, and the like at temperatures from about −50° C. to about 65° C. to give a compound of formula (46). Alternatively, a compound of formula (46) can be prepared from compounds of formulas (6), (10), (13), (15), (19), (22), (25), and (33) by reaction with a compound of formula (35) in the presence of a suitable coupling agent such as, for example, 1,1'-carbonyldiimidazole, N,N'-dicyclohexylcarbodiimide, and the like in a suitable solvent such as, for example, tetrahydrofuran, dichloromethane, and the like at temperatures from about −80° C. to about 65° C. A compound of formula (46) can be allowed to react with a sulfurating reagent such as, for example, $P_4S_{10}$ or Lawesson's reagent in a suitable solvent such as, for example, tetrahydrofuran, tert-butylmethyl ether, and the like at temperatures from about −20° C. to about 150° C. to give a compound of formula (47).

Alternatively, compounds of formulas (6), (10), (13), (15), (19), (22), (25), and (33) can be allowed to react with a compound of formula (38) in the presence of a suitable base such as, for example, triethylamine, ethyldiisopropylamine, and the like in a suitable solvent such as, for example, dichloromethane, diethyl ether, tetrahydrofuran, and the like at temperatures from about −50° C. to about 65° C. to give a compound of formula (48). A compound of formula (48) can be allowed to react with a sulfurating reagent such as, for example, $P_4S_{10}$ or Lawesson's reagent in a suitable solvent such as, for example, tetrahydrofuran, tert-butylmethyl ether, and the like at temperatures from about −20° C. to about 150° C. to give a compound of formula (49).

Alternatively, compounds of formulas (6), (10), (13), (15), (19), (22), (25), and (33) can be allowed to react with a compound of formula (50) for $R^6$ not equal to hydrogen, prepared by allowing a compound of formula (51) to react with a suitable acylating reagent such as, for example, phosgene, diphosgene, triphosgene, 4-nitrophenyl chloroformate, and the like with or without the presence of a suitable base such as, for example, triethylamine, ethyldiisopropylamine, and the like in a suitable solvent such as, for example, dichloromethane, diethyl ether, tetrahydrofuran, and the like at temperatures from about −50° C. to about 95° C., in the presence of a suitable base such as, for example, triethylamine, ethyldiisopropylamine, and the like in a suitable solvent such as, for example, dichloromethane, diethyl ether, tetrahydrofuran, and the like at temperatures from about −50° C. to about 65° C. to give a compound of formula (53). Alternatively, a compound of formula (53) wherein $R^6$ equals hydrogen can be prepared by allowing the reaction of compounds of formula (6), (10), (13), (15), (19), (22), (25), and (33) with a compound of formula (52) in a suitable solvent such as, for example, dichloromethane, diethyl ether, tetrahydrofuran, and the like with or without the presence of a suitable catalyst such as, for example, 4-dimethylamino-pyridine, tributylphosphine, and the like at temperatures from about −50° C. to about 95° C. A compound of formula (53) can be allowed to react with a sulfurating reagent such as, for example, $P_4S_{10}$ or Lawesson's reagent in a suitable solvent such as, for example, tetrahydrofuran, tert-butylmethyl ether, and the like at temperatures from about −20° C. to about 150° C. to give a compound of formula (54).

Compounds of formulas (56), (57), (59), (60), (62), and (64) wherein X is —$NR^6$—CO—, —O—CO—, —CO—, —$NR^6$—CS—, —O—CS—, or —CO—$CH_2$— can be prepared as set forth in Scheme 6.

In Scheme 6, compounds of formulas (6), (10), (13), (15), (19), (22), (25), and (33) wherein $R^{8a}$ equals $HOCH_2$— can be allowed to react with an oxidizing agent such as, for example, manganese dioxide, potassium permanganate, and the like in a suitable solvent such as, for example, tetrahydrofuran, tert-butylmethyl ether, acetone, water and the like at temperatures from about −50° C. to about 50° C. to give a compound of formula (55). A compound of formula (55) can be allowed to react with a compound of formula (51) in the presence of a suitable coupling agent such as, for example, 1,1'-carbonyldiimidazole, N,N'-dicyclohexylcarbodiimide, and the like in a suitable solvent such as, for example, tetrahydrofuran, dichloromethane, and the like at temperatures from about −80° C. to about 65° C. to give compound of formula (56). Alternatively, a compound of formula (56) can be prepared by allowing a compound of formula (55) to react with a compound of formula (50), prepared according to Scheme 5, in the presence of a suitable base such as, for example, triethylamine, ethyldiisopropylamine, and the like in a suitable solvent such as, for example, dichloromethane, diethyl ether, tetrahydrofuran, and the like at temperatures from about −50° C. to about 150° C. A compound of formula (56) can be allowed to react with a sulfurating reagent such as, for example, $P_4S_{10}$ or Lawesson's reagent in a suitable solvent such as, for example, tetrahydrofuran, tert-butylmethyl ether, and the like at temperatures from about −20° C. to about 150° C. to give a compound of formula (57).

Alternatively, a compound of formula (55) can be allowed to react with a compound of formula (58) in the presence of a suitable coupling agent such as, for example, 1,1'-carbonyldiimidazole, N,N'-dicyclohexylcarbodiimide, and the like in a suitable solvent such as, for example, tetrahydrofuran, dichloromethane, and the like at temperatures from about −80° C. to about 65° C. to give compound of formula (59). Alternatively, a compound of formula (59) can be prepared by allowing a compound of formula (55) to react with a suitable chlorinating reagent such as, for example, oxalyl chloride, thionyl chloride, and the like with or without a suitable solvent such as, for example, dichloromethane and the like at temperatures from about −20° C. to about 150° C., followed by reaction of the intermediate with a compound of formula (58). A compound of formula (59) can be allowed to react with a sulfurating reagent such as, for example, $P_4S_{10}$ or Lawesson's reagent in a suitable solvent such as, for example, tetrahydrofuran, tert-butylmethyl ether, and the like at temperatures from about −20° C. to about 150° C. to give a compound of formula (60).

Alternatively, a compound of formula (55) can be allowed to react with a suitable chlorinating reagent such as, for example, oxalyl chloride, thionyl chloride, and the like with or without a suitable solvent such as, for example, dichloromethane and the like at temperatures from about −20° C. to about 150° C., followed by reaction of the intermediate with a compound of formula (61), wherein $R^1$-M is a suitable organometallic reagent such as, for example, an organotin, organomanganesium, organozinc, organolithium, or cuprate salt, in a suitable solvent such as, for example, tetrahydrofuran, tert-butylmethyl ether, and the like at temperatures from about −100° C. to about 65° C. to give a compound of formula (62).

Alternatively, compounds of formulas (6), (10), (13), (15), (19), (22), (25), and (33) wherein $R^{8a}$ equals HOCH$_2$— can be allowed to react with a suitable brominating reagent such as, for example, phosphorous tribromide, triphenylphosphine/carbon tetrabromide, and the like in a suitable solvent such as, for example, dichloromethane, tetrahydrofuran, carbon tetrachloride, and the like at temperatures from about −50° C. to about 150° C., and the resulting intermediate can be allowed to react with potassium cyanide in a suitable solvent such as, for example, dimethylsulfoxide, dimethylformamide, and the like at temperatures from about 0° C. to about 200° C., followed by hydrolysis of the resulting nitrile using suitable conditions such as, for example, aqueous hydrochloric acid, sodium hydroxide in tetrahydrofuran, or methanol/hydrogen chloride gas and water to give a compound of formula (63). Alternatively, a compound of formula (63) can be prepared by allowing compounds of formulas (6), (10), (13), (15), (19), (22), (25), and (33) wherein $R^{8a}$ equals HOCH$_2$— to react with a suitable brominating reagent such as, for example, phosphorous tribromide, triphenylphosphine/carbon tetrabromide, and the like in a suitable solvent such as, for example, dichloromethane, tetrahydrofuran, carbon tetrachloride, and the like at temperatures from about −50° C. to about 150° C., and the resulting intermediate can be allowed to react with a suitable metallating agent such as, for example, n-butyl lithium or magnesium metal in a suitable solvent such as, for example, tetrahydrofuran, tert-butylmethyl ether, and the like at temperatures from about −100° C. to about 65° C., and the resulting anion can be allowed to react with a source of carbon dioxide such as, for example, dry ice and the like at temperatures from about −80° C. to about 25° C. A compound of formula (63) can be allowed to react with a suitable chlorinating reagent such as, for example, oxalyl chloride, thionyl chloride, and the like with or without a suitable solvent such as, for example, dichloromethane and the like at temperatures from about −20° C. to about 150° C., followed by reaction of the intermediate with a compound of formula (61), wherein $R^1$-M is a described above, to give a compound of formula (64).

Compounds of Formula I wherein $R^1$, $R^2$, $R^{2a}$, $R^3$, $R^{3a}$, $R^4$, X, Z, and m are as defined above can be prepared as set forth in Scheme 7.

In Scheme 7, compounds of formulas (36), (37), (39), (40), (44), (45), (46), (47), (48), (49), (53), (54), (56), (57), (59), (60), (62), and (64) can be selectively deprotected and. the resulting carboxylic acids resolved into their individual stereoisomers by methods known to one skilled in the art to give a compound of formula (65). A compound of formula (65) can be allowed to react with a compound of formula (66) in a suitable solvent such as, for example, tetrahydrofuran, ethanol, and the like with or without the presence of a suitable base such as, for example, triethylamine, sodium carbonate, and the like at temperatures from about 0° C. to about 110° C. to give a compound of formula (Ia).

A compound of formula (Ia) can be allowed to cyclize in the presence of a suitable catalyst such as, for example, para-toluenesulfonic acid, hydrogen chloride gas, titanium tetrachloride, and the like in a suitable solvent such as, for example, toluene, dichloromethane, and the like at temperatures from about −50° C. to about 150° C. to give a compound of formula (67). A compound of formula (67) can be allowed to react with a compound of formula (68) in a suitable solvent such as, for example, tetrahydrofuran, toluene, dichloromethane and the like with or without the presence of a suitable acid catalyst such as, for example, para-toluenesulfonic acid, sulfuric acid, titanium tetrachloride, titanium(IV)-dichlorodiisopropoxide and the like, or in the presence of a suitable base such as, for example, sodium hydride, lithium diisopropylamide, and the like at temperatures from about −80° C. to about 150° C. to give a compound of formula (Ib).

Alternatively, a compound of formula (65) can be allowed to react with a suitable sulfurating agent such as, for example, hydrogen sulfide and the like in the presence of a suitable coupling agent such as, for example, 1,1'-carbonyldiimidazole, N,N'-dicyclohexylcarbodiimide, and the like in a suitable solvent such as, for example, tetrahydrofuran, dichloromethane, and the like at temperatures from about −80° C. to about 65° C., followed by reaction of the resulting product with a compound of formula (66) in a suitable solvent such as, for example, tetrahydrofuran, ethanol, and the like with or without the presence of a suitable base such as, for example, triethylamine, sodium carbonate, and the like at temperatures from about 0° C. to about 110° C. to give compound of formula (Ic).

Alternatively, a compound of formula (65) can be allowed to react with a suitable reducing agent such as, for example, sodium borohydride, sodium cyanoborohydride, lithium aluminumhydride and the like in a suitable solvent such as, for example, ethanol, tetrahydrofuran, toluene, and the like, and the resulting compound can be per-silated using an excess of a suitable silylating reagent such as, for example, chlorotrimethylsilane, chloro tert-butyl-dimethylsilane, and the like, in the presence of an excess of a suitable catalyst such as, for example, imidazole, N-methylimidazole, and the like in a suitable solvent such as, for example, dimethylformamide, tetrahydrofuran, and the like, and the resulting O-silyl alcohol, O-silyl ester can be reacted with a suitable fluorinating reagent such as, for example, diethylamino sulfur trifluoride (DAST) and the like in a suitable solvent such as, for example, dichloromethane, chloroform, and the like at temperatures from about −50° C. to about 150° C., and the resulting ester can be deprotected using a suitable fluoride reagent such as, for example, tetrabutylamonium fluoride and the like in a suitable solvent such as, for example, tetrahydrofuran, dichloromethane, and the like at temperatures from about −20° C. to about 120° C. or using suitable hydrolysis conditions such as, for example, sodium hydroxide in tetrahydrofuran and the like to give a compound of formula (Id). A compound of formula (Id) can be allowed to react with a compound of formula (68) or a suitable sulfurating agent such as, for example, hydrogen sulfide and the like in the presence of a suitable coupling agent such as, for example 1,1'-carbonyldiimidazole, N,N'-dicyclohexylcarbodiimide, and the like in a suitable solvent such as, for example, tetrahydrofuran, dichloromethane, and the like at temperatures from about −80° C. to about 65° C. to give a compound of formula (Ie).

Alternatively, compounds of formulas (36), (37), (39), (40), (44), (45), (46), (47), (48), (49), (53), (54), (56), (57), (59), (60), (62), and (64) can be allowed to react with a suitable fluorinating reagent such as, for example, diethylamino sulfur trifluoride (DAST) and the like in a suitable solvent such as, for example, dichloromethane, chloroform, and the like at temperatures from about −50° C. to about 150° C., and the resulting ester can be selectively deprotected using a suitable method known to one skilled in the art, and the resulting carboxylic acid can be resolved into its individual stereoisomers using a suitable method known to one skilled in the art, to give a compound of formula (If). A compound of formula (If) can be allowed to react with a compound of formula (68) or a suitable sulfurating agent such as, for example, hydrogen sulfide and the like in the presence of a suitable coupling agent such as, for example 1,1'-carbonyldiimidazole, N,N'-dicyclohexylcarbodiimide, and the like in a suitable solvent such as, for example, tetrahydrofuran, dichloromethane, and the like at temperatures from about −80° C. to about 65° C. to give a compound of formula (Ig).

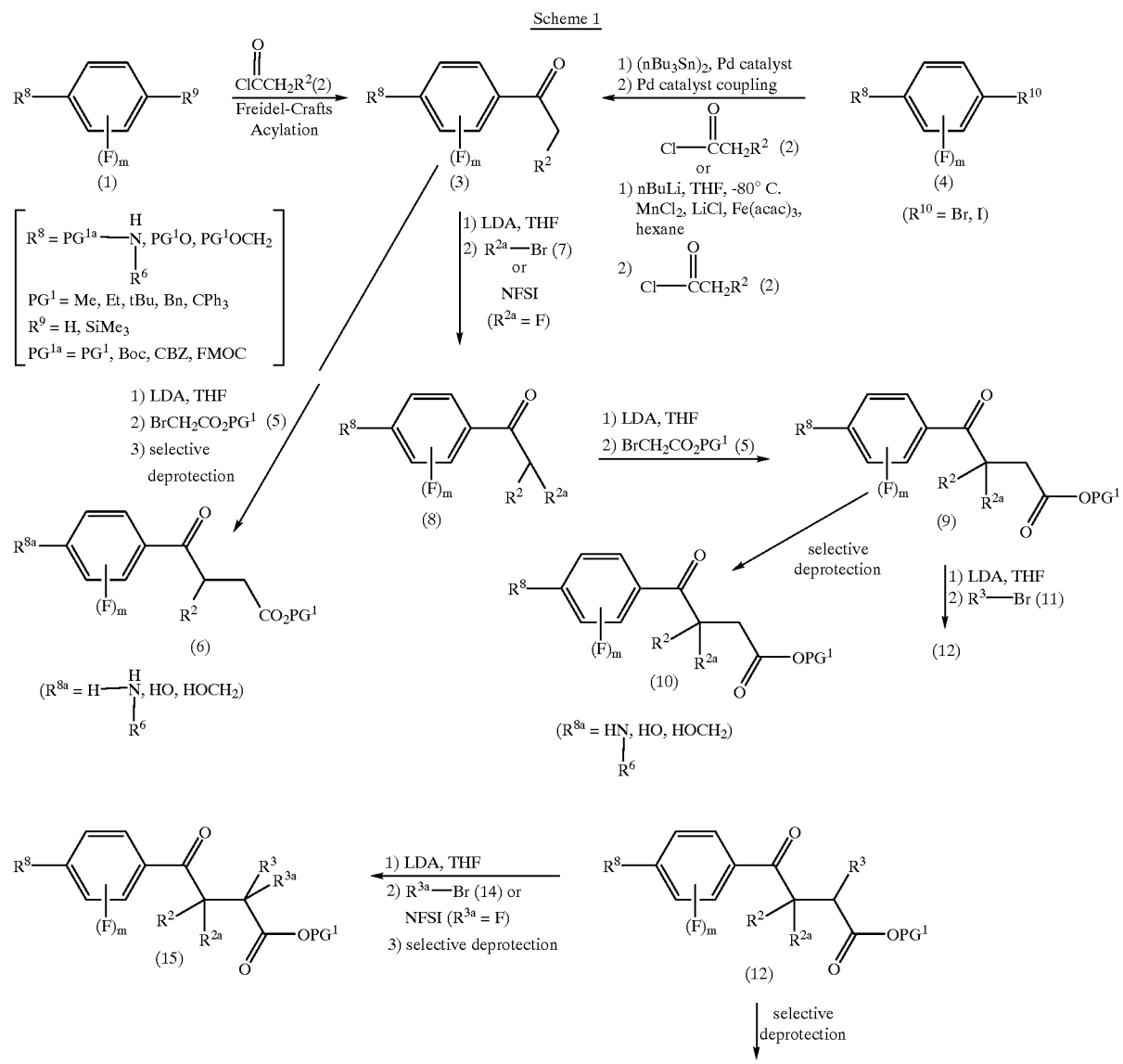

Scheme 1

-continued
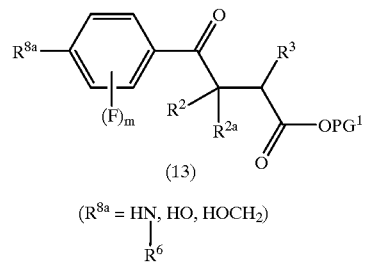
Scheme 2
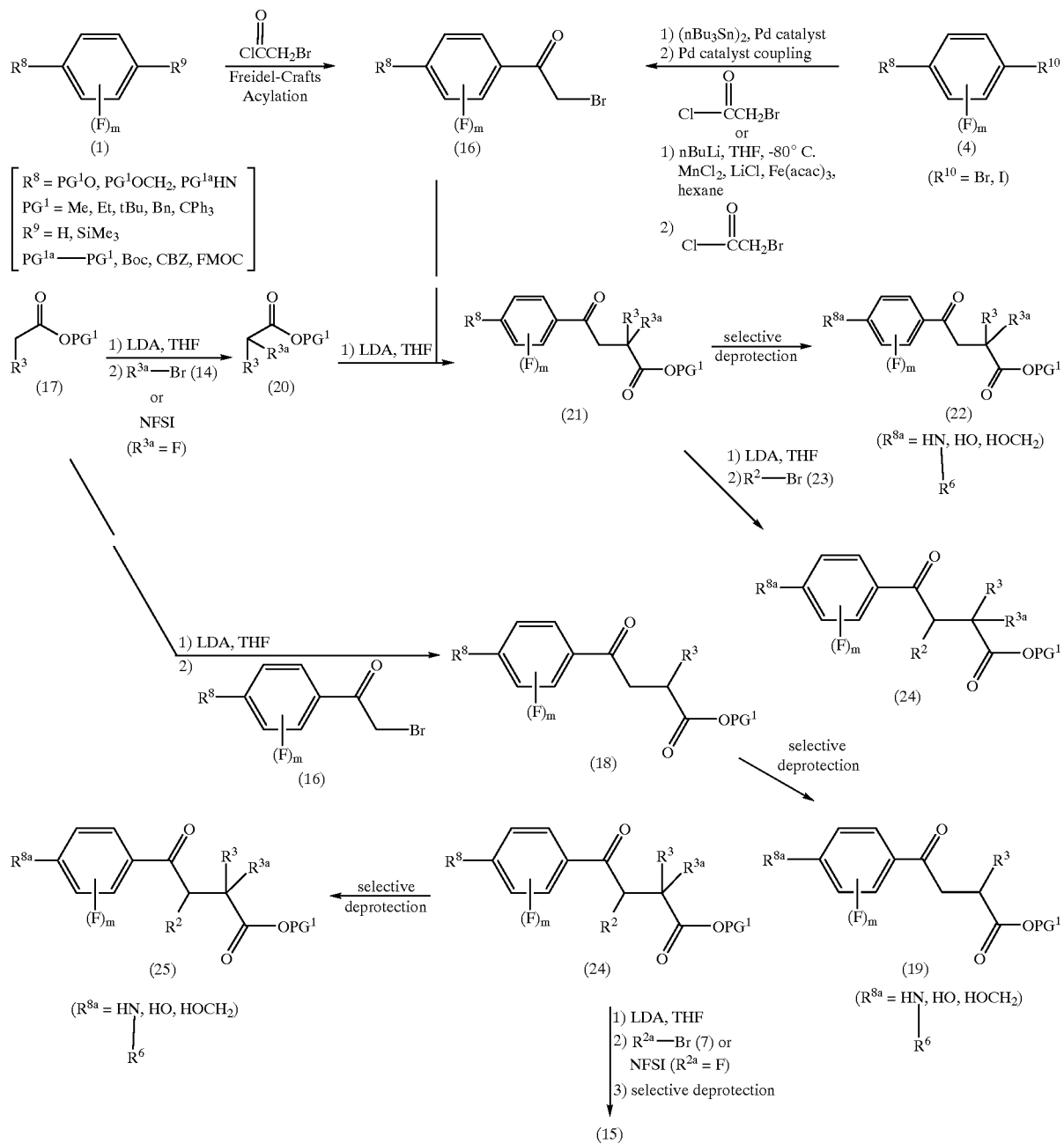

Scheme 3
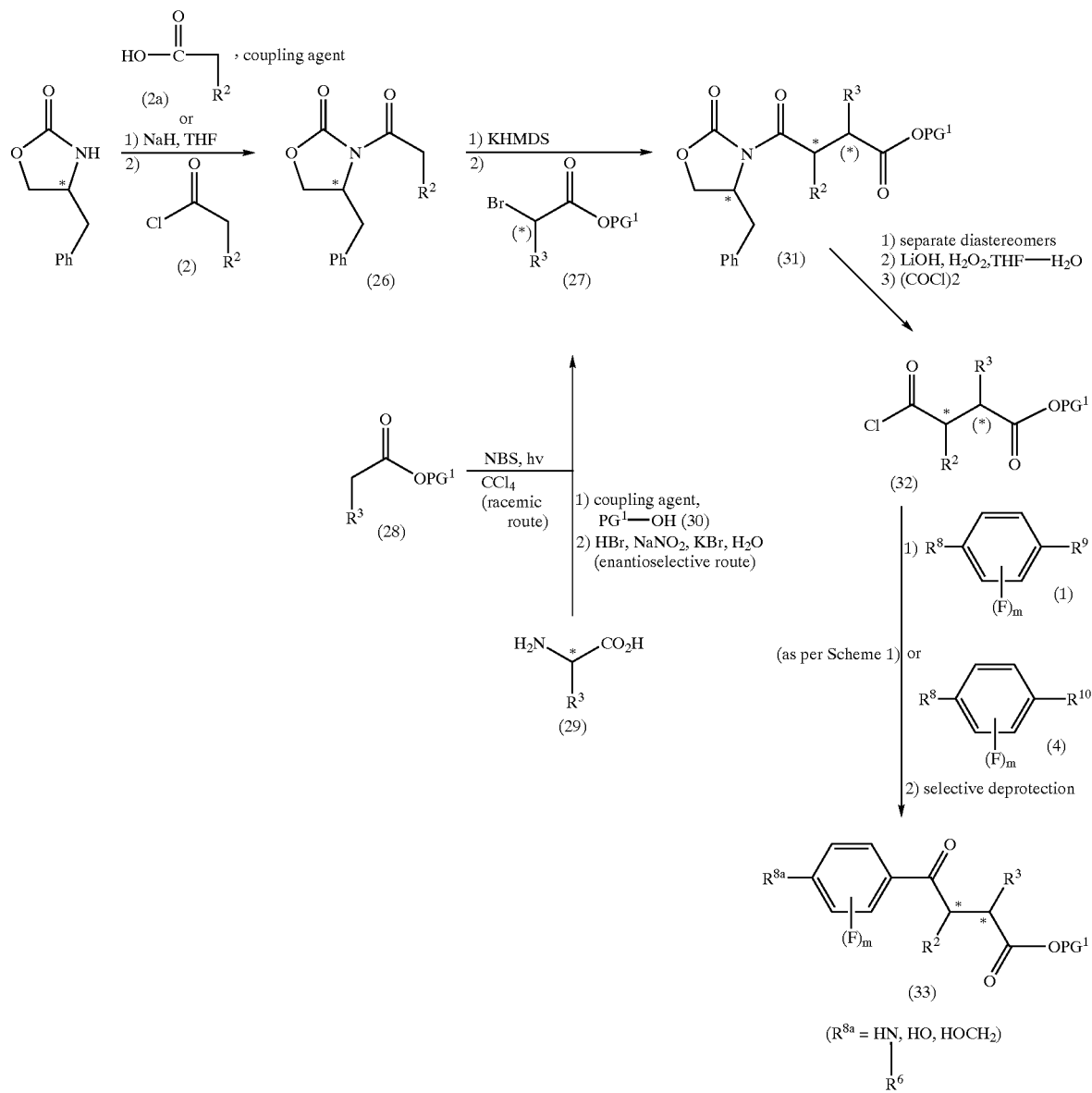
Scheme 4
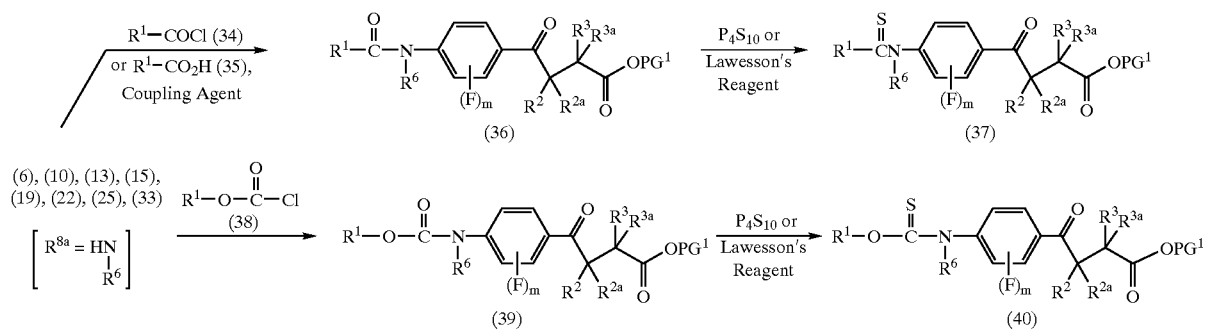

-continued
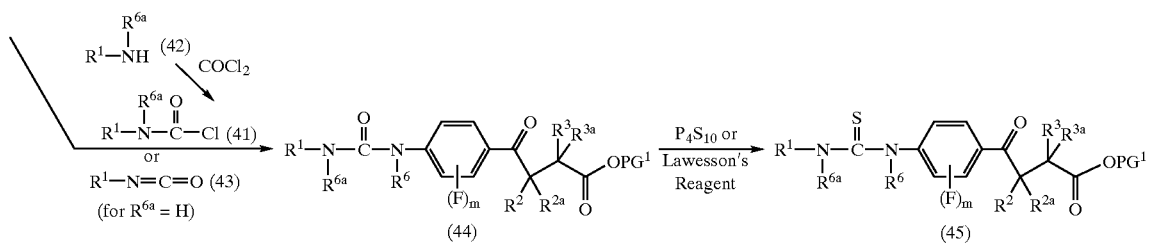
Scheme 5
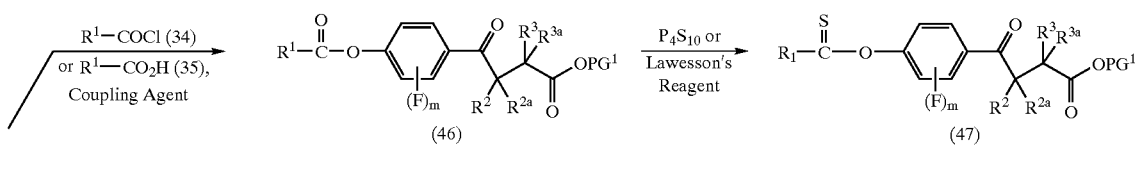
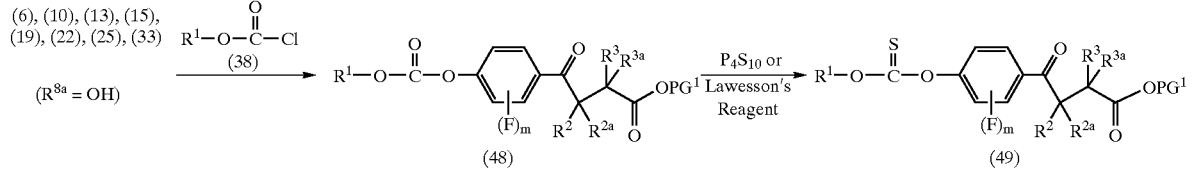
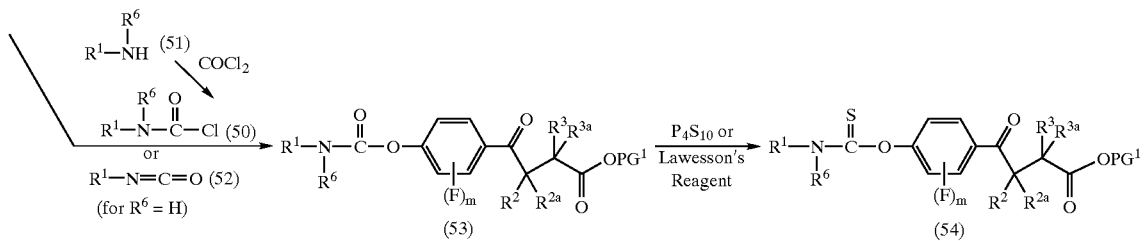

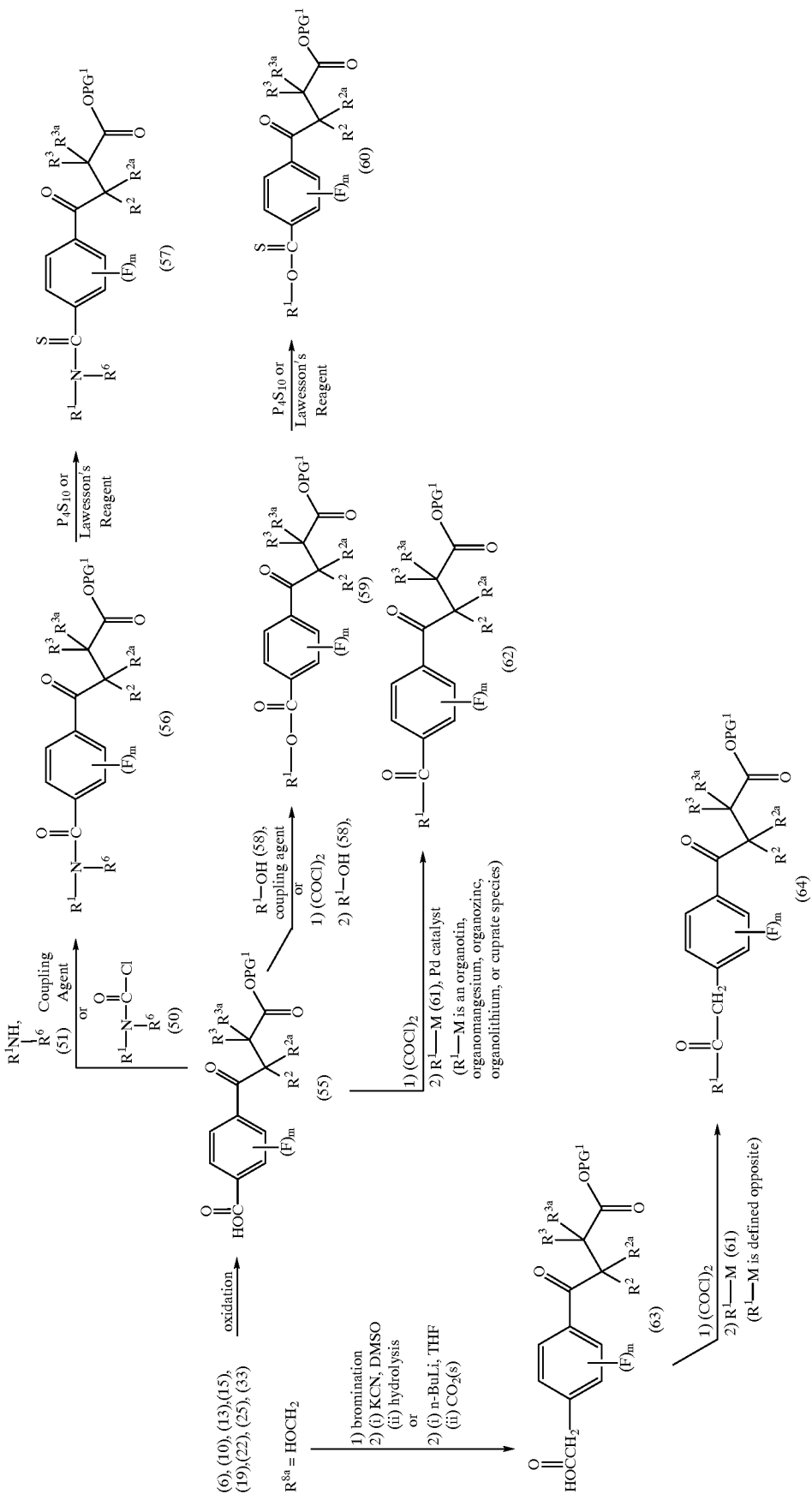

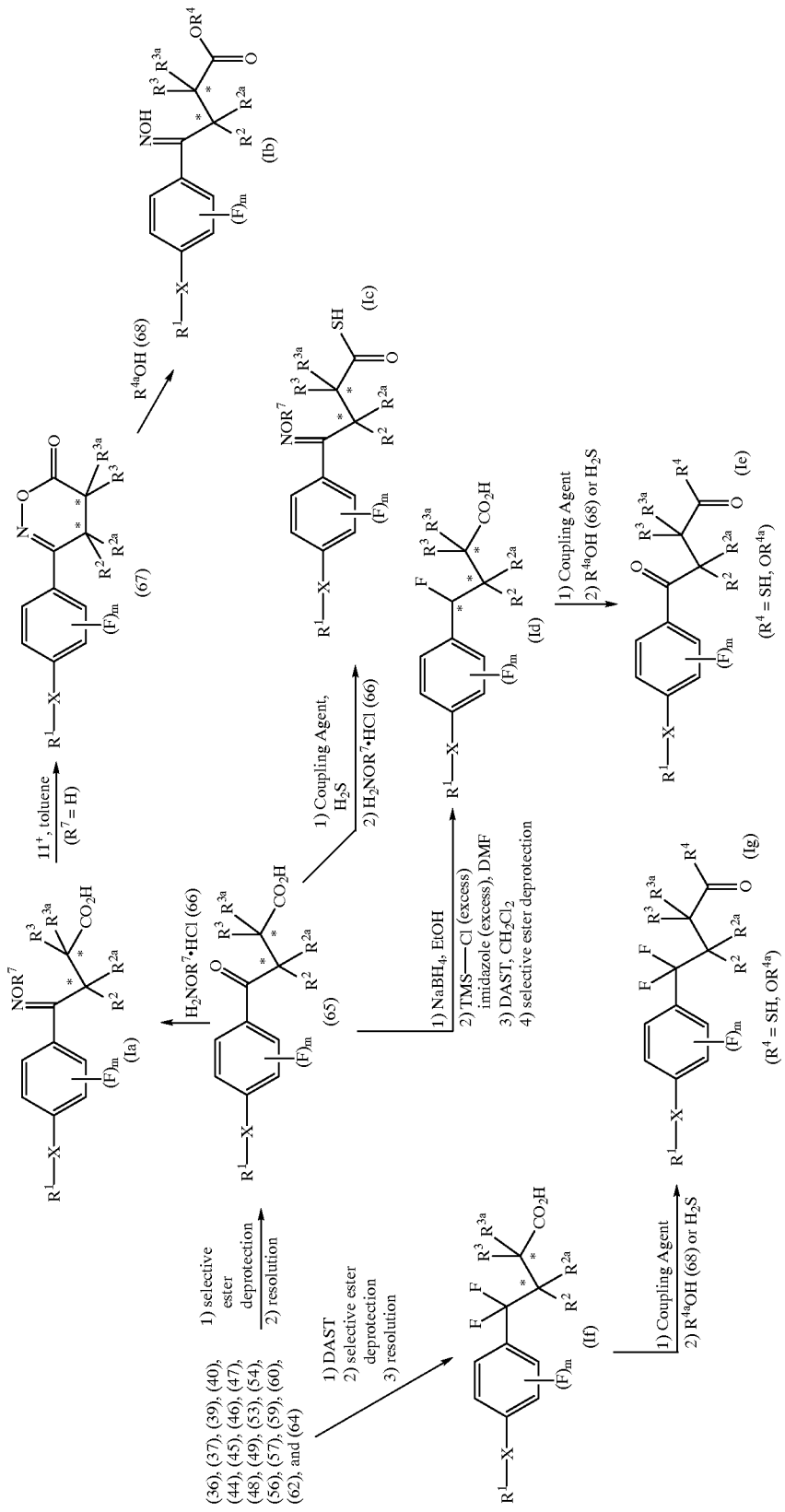

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, left ventricular dilation, restenosis, periodontal disease, corneal ulceration, treatment of burns, decubital ulcers, wound healing, cancer, inflammation, pain, arthritis, osteoporosis, renal disease, or other autoimmune or inflammatory disorders dependent upon tissue invasion by leukocytes, or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy, the compounds utilized in the pharmaceutical methods of the invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

4-[4-(4-Methyl-benzoylamino)-phenyl]-4-oxo-butyric acid

Step (a) Preparation of 4-(4-Acetylamino-phenyl)-4-oxo-butyric acid

To a flask charged with anhydrous aluminum chloride (128.1 g, 0.961 mol) was added dropwise neat dimethylformamide (21 mL, 0.27 mol) at a rate such that the internal temperature remained below 70° C. The resulting mixture was thoroughly mixed. To the stirred thick mixture was added in ten portions a mixture of acetanilide (13.53 g, 0.100 mol) and succinic anhydride (10.01 g, 0.100 mol) that had been preground together with a mortar and pestle. The addition rate was controlled to keep the internal temperature at less than or equal to 72° C. The resulting mixture was stirred at 65° C. to 70° C. for 1.25 hours, then poured hot onto ice (1.0 kg). The mixture was acidified with concentrated hydrochloric acid (60 mL), and the resulting solids were filtered. The filtercake was washed with 0.05 M hydrocloric acid and allowed to air dry overnight. The filtercake was suspended in hot water (93 mL), methanol (120 mL) was added, and the hot cloudy solution was gravity filtered. The filtrate was boiled down to 100 mL volume and allowed to cool. The solids were filtered, washed with water-methanol, and dried in vacuo to give 10.03 g of 4-(4-acetylamino-phenyl)-4-oxo-butyric acid as a tan solid.

$^1$H-NMR (DMSO-d$_6$) δ2.03 (s, 3H), 2.50 (m, 2H), 3.13 (m, 2H), 7.66 (d, 2H), 7.88 (d, 2H), 10.24 (br s, 1H), 12.08 (br s, 1H) ppm.

Step (b) Preparation of 4-(4-Amino-phenyl)-4-oxo-butyric acid

A suspension of 4-(4-acetylamino-phenyl)-4-oxo-butyric acid (9.84 g, 0.0418 mol) in 1.0 M hydrocloric acid (125 mL) was heated on a steam bath for 1.5 hours, gravity filtered hot, and the filtrate allowed to cool. To the stirred solution was added 50% wt/wt sodium hydroxide (9.7 g) dropwise until pH equaled 3 to 4. The resulting precipitate was filtered, and the filtercake was washed with very dilute hydrochloric acid. The procedure was repeated on the solids with fresh 1.0 M hydrochloric acid (100 mL) to give 7.00 g of 4-(4-amino-phenyl)-4-oxo-butyric acid as a tan solid.

$^1$H-NMR (DMSO-d$_6$) δ2.45 (m, 2H), 3.00 (m, 2H), 5.98 (s, 2H), 6.50 (d, 2H), 7.63 (d, 2H), 11.99 (br s, 1H) ppm.

Step (c) Preparation of 4-(4-Amino-phenyl)-4-oxo-butyric acid, methyl ester

To a stirred, partial solution of 4-(4-amino-phenyl)-4-oxo-butyric acid (6.96 g, 0.0360 mol) in toluene (240 mL) and methanol (240 mL) at room temperature under nitrogen was added dropwise over 30 minutes a 2.0 M solution of trimethylsilyldiazomethane in hexanes (18 mL, 0.036 mol), and the mixture was stirred for 22 hours. Additional 2.0 M solution of trimethylsilyldiazomethane in hexanes (12 mL, 0.024 mol) was added dropwise, and the mixture was stirred overnight. Additional 2.0 M solution of trimethylsilyldiazomethane in hexanes (19 mL, 0.038 mol) was added dropwise, and the mixture was stirred overnight. After a total of 3 days, the mixture was rotary evaporated, and the residue was suspended in tetrahydrofuran (200 mL) and dichloromethane (100 mL). The mixture was washed with 0.1 M aqueous sodium hydroxide, water, brine, and dried (Na$_2$SO$_4$). The solution was rotary evaporated to give a solid, which was crystallized from chloroform to give 5.13 g of 4-(4-amino-phenyl)-4-oxo-butyric acid, methyl ester as a tan solid; mp 160–162° C.

Step (d) Preparation of 4-[4-(4-Methyl-benzoylamino)-phenyl]-4-oxo-butyric acid, methyl ester A mixture of 4-methyl-benzoyl chloride (0.74 mL, 0.0056 mol) and 4-(4-amino-phenyl)-4-oxo-butyric acid, methyl ester (0.93 g, 0.0045 mol) in toluene (22 mL) was refluxed under nitrogen for 17 hours and allowed to cool. The mixture was diluted with THF (20 mL), and washed with 0.1 M aqueous sodium hydroxide. The solids that remained undissolved were filtered, washed with water, and dried in house vacuum (40° C., air bleed) to give 0.592 g of 4-[4-(4methyl-benzoylamino)-phenyl]-4-oxo-butyric acid, methyl ester as an off-white solid; mp 192–195° C.

Step (e) Preparation of 4-[4-(4-Methyl-benzoylamino)-phenyl]-4-oxo-butyric acid

To a stirred, partial solution of 4-[4-(4-methyl-benzoylamino)-phenyl]-4-oxo-butyric acid, methyl ester (0.5748 g, 0.00177 mol) in THF (11 mL) was added 1.0 M NaOH (3.7 mL, 0.0037 mol), and the mixture was stirred overnight. The resulting suspension was filtered, and the filtercake was washed with THF. The solids were partitioned between EtOAc-THF and 0.2 M HCl, and left for 8 days. The solids were filtered, washed with water, and dried in vacuo to give 0.2133 g of 4-[4-(4-methyl-benzoylamino)-phenyl]-4-oxo-butyric acid as an off-white solid; mp 257–258° C.

EXAMPLE 2

4-Hydroxyimino-4-[(4-methyl-benzoyl)amino-phenyl]-butyric acid

A stirred mixture of 4-[4-(4-methyl-benzoylamino)-phenyl]-4-oxo-butyric acid (0.1038 g, 0.000333 mol) (Example 1), hydroxylamine hydrochloride (0.0278 g, 0.00040 mol), and sodium carbonate (0.0424 g, 0.00040 mol) in absolute ethanol (2 mL) was refluxed under nitrogen for 54 hours and allowed to cool. The resulting suspension was filtered, and the filtrate was rotary evaporated. The residue was combined with the filtercake, and the mixture was dissolved in methanol-water (4:3, 5 mL). Added 1.0 M HCl (0.6d0 mL) to a pH equal to 2, and filtered the precipitate. The filtercake was washed. The filtrate and washings were combined, silica gel (1.2 g) was added, and the mixture was rotary evaporated to dryness. The powder was purified by chromatography on silica gel (15 g, 230–400 mesh), eluting with dichloromethane-methanol (14:1, 16×10 mL), then (10:1, 25×20 mL) to give 4-hydroxyimino-4-[(4-methyl-benzoyl)amino-phenyl]-butyric acid as a pale yellow solid; mp 165–168° C.

EXAMPLE 3

4-Oxo-4-(4-pentanoylamino-phenyl)-butyric acid

To a 2-dram vial was added pentanoyl chloride (0.040 mL, 0.00033 mol), 4-(4-amino-phenyl)-4-oxo-butyric acid, methyl ester (0.051 g, 0.00025 mol) (Example 1, Step (c)), dichloromethane (3 mL), and a 3.6 mmol amine per gram of 4-morpholinomethyl polystyrene resin (0.10 g, 0.00036 mol amine), the vial was tightly capped, and the mixture was shaken at room temperature for approximately 5 hours. To the mixture was added an excess of [Bis(2-aminoethyl) amino-ethyl]amino-methyl polystyrene resin, the vial was tightly capped, and the mixture was shaken at room temperature overnight. The mixture was gravity filtered into a clean 2-dram vial, and the solvent evaporated under a stream of nitrogen. The residue was dissolved in THF (3 mL), 1.0 M NaOH (0.5 mL, 0.0005 mol) was added, and the mixture was shaken overnight. Additional 1.0 M NaOH (0.25 mL, 0.00025 mol) was added, and the mixture was shaken overnight. To the mixture was added 1.0 M HCl (1.0 mL, 0.001 mol), and the two-phase mixture was shaken for 1 hour. The bottom layer was withdrawn by pipet, and the remaining organics were evaporated under a stream of nitrogen. The residue was dried in vacuo to give 0.054 g of 4-oxo-4-(4-pentanoylamino-phenyl)-butyric acid as a pink solid; mp 153–155° C.

EXAMPLE 4

4-[4-(3-Fluoro-benzoylamino)-phenyl]-4-oxo-butyric acid

In a manner similar to that described in Example 3, 3-fluorobenzoyl chloride (0.053 g, 0.00033 mol) was allowed to react with 4-(4-amino-phenyl)-4-oxo-butyric acid, methyl ester (0.052 g, 0.00025 mol) (Example 1, Step (c)), and the resulting intermediate was hydrolyzed to give 0.0331 g of 4-[4-(3-fluoro-benzoylamino)-phenyl]-4-oxo-butyric acid as an off-white solid; mp 239–241° C.

EXAMPLE 5

4-[4-(2-Fluoro-benzoylamino)-phenyl]-4-oxo-butyric acid

In a manner similar to that described in Example 3, 2-fluorobenzoyl chloride (0.053 g, 0.00033 mol) was allowed to react with 4-(4-amino-phenyl)-4-oxo-butyric acid, methyl ester (0.052 g, 0.00025 mol) (Example 1, Step (c)), and the resulting intermediate was hydrolyzed to give 0.0438 g of 4-[4-(2-fluoro-benzoylamino)-phenyl]-4-oxo-butyric acid as an off-white solid; mp 191–193° C.

EXAMPLE 6

4-[4-(4-Fluoro-benzoylamino)-phenyl]-4-oxo-butyric acid

In a manner similar to that described in Example 3, 4-fluorobenzoyl chloride (0.053 g, 0.00033 mol) was allowed to react with 4-(4-amino-phenyl)-4-oxo-butyric acid, methyl ester (0.052 g, 0.00025 mol) (Example 1, Step (c)), and the resulting intermediate was hydrolyzed to give 0.0219 g of 4-[4-(4-fluoro-benzoylamino)-phenyl]-4-oxo-butyric acid as an off-white solid; mp 253–255.° C.

EXAMPLE 7

4-[4-(Cyclohexane-carbonyllamino)-phenyl]-4-oxo-butyric acid

In a manner similar to that described in Example 3, cyclohexanecarbonyl chloride (0.048 g, 0.00033 mol) was allowed to react with 4-(4-amino-phenyl)-4-oxo-butyric acid, methyl ester (0.052 g, 0.00025 mol) (Example 1, Step (c)), and the resulting intermediate was hydrolyzed to give 0.086 g of 4-[4-(cyclohexane-carbonyl]amino)-phenyl]-4-oxo-butyric acid as an off-white solid; mp 195–198° C.

EXAMPLE 8

4-[4-(Pyridin-3-yl-carbonylamino)-phenyl]-4-oxo-butyric acid

In a manner similar to that described in Example 3, 3-pyridinecarbonyl chloride (0.066 g, 0.00039 mol) was allowed to react with 4-(4-amino-phenyl)-4-oxo-butyric acid, methyl ester (0.052 g, 0.00025 mol) (Example 1, Step (c)), and the resulting intermediate was hydrolyzed to give 0.003 g of 4-[4-((pyridin-3-yl)-carbonylamino)-phenyl]-4-oxo-butyric acid as a yellow solid; MS-(AP+) MH$^+$299.

EXAMPLE 9

4-[4-(Nonanoylamino)-phenyl]-4-oxo-butyric acid

In a manner similar to that described in Example 3, nonanoyl chloride (0.055 g, 0.00031 mol) was allowed to react with 4-(4-amino-phenyl)-4-oxo-butyric acid, methyl ester (0.052 g, 0.00025 mol), and the resulting intermediate was hydrolyzed to give 0.055 g of 4-[4-(nonanoylamino)-phenyl]-4-oxo-butyric acid as an off-white solid; MS-(AP+) MH$^+$334.

EXAMPLE 10

4-[4-(Octanoylamino)-phenyl]-4-oxo-butyric acid

In a manner similar to that described in Example 3, octanoyl chloride (0.063 g, 0.00034 mol) was allowed to react with 4-(4-amino-phenyl)-4-oxo-butyric acid, methyl ester (0.052 g, 0.00025 mol), and the resulting intermediate was hydrolyzed to give 0.063 g of 4-[4-(octanoylamino)-phenyl]-4-oxo-butyric acid as an off-white solid; MS-(AP+) MH$^+$320.

EXAMPLE 11

4-Oxo-4-[4-(Propionylamino)-phenyl]-butyric acid

In a manner similar to that described in Example 3, propionyl chloride (0.029 g, 0.00032 mol) was allowed to react with 4-(4-amino-phenyl)-4-oxo-butyric acid, methyl ester (0.052 g, 0.00025 mol), and the resulting intermediate was hydrolyzed to give 0.027 g of 4-oxo-4-[4-(propionylamino)-phenyl]-butyric acid as an off-white solid; MS-(AP+) MH$^+$250.

EXAMPLE 12

4-[4-(3-Methoxy-benzoylamino)-phenyl]-4-oxo-butyric acid

In a manner similar to that described in Example 3, 3-methoxybenzoyl chloride (0.052 g, 0.00030 mol) was allowed to react with 4-(4-amino-phenyl)-4-oxo-butyric acid, methyl ester (0.052 g, 0.00025 mol), and the resulting intermediate was hydrolyzed to give 0.069 g of 4-[4-(3-methoxy-benzoylamino)-phenyl]-4-oxo-butyric acid as an off-white solid; MS-(AP+) MH$^+$328.

EXAMPLE 13

4-[4-(2,4-Dichloro-benzoylamino)-phenyl]-4-oxo-butyric acid

In a manner similar to that described in Example 3, 2,4-dichloro-benzoyl chloride (0.070 g, 0.00033 mol) was allowed to react with 4-(4-amino-phenyl)-4-oxo-butyric acid, methyl ester (0.052 g, 0.00025 mol), and the resulting intermediate was hydrolyzed to give 0.006 g of 4-[4-(2,4-dichloro-benzoylamino)-phenyl]-4-oxo-butyric acid as a yellow solid; MS-(AP+) MH$^+$366.

EXAMPLE 14

4-{4-[4-(4-Bromo-phenyl)-butyrylamino]-phenyl}-4-oxo-butyric acid

In a manner similar to that described in Example 3, 4-(4-bromo-phenyl)-butyryl chloride (0.086 g, 0.00033 mol) was allowed to react with 4-(4-amino-phenyl)-4-oxo-butyric acid, methyl ester (0.052 g, 0.00025 mol), and the resulting intermediate was hydrolyzed to give 0.089 g of 4-{4-[4-(4-bromo-phenyl)-butyrylamino]-phenyl}-4-oxo-butyric acid as a yellow solid; MS-(AP+) MH$^+$419.

EXAMPLE 15

4-[4-(Heptanoylamino)-phenyl]-4-oxo-butyric acid

In a manner similar to that described in Example 3, heptanoyl chloride (0.051 g, 0.00034 mol) was allowed to react with 4-(4-amino-phenyl)-4-oxo-butyric acid, methyl ester (0.052 g, 0.00025 mol), and the resulting intermediate was hydrolyzed to give 0.048 g of 4-[4-(heptanoylamino)-phenyl]-4-oxo-butyric acid as an off-white solid; MS-(AP+) MH$^+$306.

EXAMPLE 16

4-[4-(4-Ethyl-benzoylamino)-phenyl]-4-oxo-butyric acid

In a manner similar to that described in Example 3, 4-ethyl-benzoyl chloride (0.057 g, 0.00034 mol) was allowed to react with 4-(4-amino-phenyl)-4-oxo-butyric acid, methyl ester (0.052 g, 0.00025 mol), and the resulting intermediate was hydrolyzed to give 0.023 g of 4-[4-(4-ethyl-benzoylamino)-phenyl]-4-oxo-butyric acid as an off-white solid; MS-(AP+) MH$^+$326.

EXAMPLE 17

4-[4-(4-Butoxy-benzoylamino)-phenyl]-4-oxo-butyric acid

In a manner similar to that described in Example 3, 4-butoxy-benzoyl chloride (0.073 g, 0.00034 mol) was allowed to react with 4-(4-amino-phenyl)-4-oxo-butyric acid, methyl ester (0.052 g, 0.00025 mol), and the resulting intermediate was hydrolyzed to give 0.051 g of 4-[4-(4-butoxy-benzoylamino)-phenyl]-4-oxo-butyric acid as an off-white solid; MS-(AP+) MH$^+$370.

EXAMPLE 18

4-[4-(4-Chloro-3-nitro-benzoylamino)-phenyl]-4-oxo-butyric acid

In a manner similar to that described in Example 3, 4-chloro-3-nitro-benzoyl chloride (0.073 g, 0.00033 mol) was allowed to react with 4-(4-amino-phenyl)-4-oxo-butyric acid, methyl ester (0.052 g, 0.00025 mol), and the resulting intermediate was hydrolyzed to give 0.045 g of 4-[4-(4-chloro-3-nitro-benzoylamino)-phenyl]-4-oxo-butyric acid as a yellow solid; MS-(AP+) MH$^+$377.

EXAMPLE 19

4-[4-(Cinnamoylamino)-phenyl]-4-oxo-butyric acid

In a manner similar to that described in Example 3, cinnamoyl chloride (0.057 g, 0.00034 mol) was allowed to react with 4-(4-amino-phenyl)-4-oxo-butyric acid, methyl ester (0.052 g, 0.00025 mol), and the resulting intermediate was hydrolyzed to give 0.049 g of 4-[4-(cinnamnoylamino)-phenyl]-4-oxo-butyric acid as a yellow solid; MS-(AP+) MH$^+$324.

EXAMPLE 20

4-[4-(4-Bromo-benzoylamino)-phenyl]-4-oxo-butyric acid

In a manner similar to that described in Example 3, 4-bromo-benzoyl chloride (0.070 g, 0.00032 mol) was allowed to react with 4-(4-amino-phenyl)-4-oxo-butyric acid, methyl ester (0.052 g, 0.00025 mol), and the resulting intermediate was hydrolyzed to give 0.021 g of 4-[4-(4-bromo-benzoylamino)-phenyl]-4-oxo-butyric acid as a yellow solid; MS-(AP+) MH$^+$376.

EXAMPLE 21

4-[4-(3-Nitro-benzoylamino)-phenyl]-4-oxo-butyric acid

In a manner similar to that described in Example 3, 3-nitro-benzoyl chloride (0.064 g, 0.00035 mol) was allowed to react with 4-(4-amino-phenyl)-4-oxo-butyric acid, methyl ester (0.052 g, 0.00025 mol), and the resulting intermediate was hydrolyzed to give 0.022 g of 4-[4-(3-nitro-benzoylamino)-phenyl]-4-oxo-butyric acid as a yellow solid; MS-(AP+) MH$^+$343.

EXAMPLE 22

4-[4-(Butyrylamino)-phenyl]-4-oxo-butyric acid

In a manner similar to that described in Example 3, butyryl chloride (0.033 g, 0.00031 mol) was allowed to react with 4-(4-amino-phenyl)-4-oxo-butyric acid, methyl ester (0.052 g, 0.00025 mol), and the resulting intermediate was hydrolyzed to give 0.042 g of 4-[4-(butyrylamino)-phenyl]-4-oxo-butyric acid as an off-white solid; MS-(AP+) MH$^+$264.

EXAMPLE 23

4-[4-(Decanoylamino)-phenyl]-4-oxo-butyric acid

In a manner similar to that described in Example 3, decanoyl chloride (0.069 g, 0.00036 mol) was allowed to react with 4-(4-amino-phenyl)-4-oxo-butyric acid, methyl ester (0.052 g, 0.00025 mol), and the resulting intermediate was hydrolyzed to give 0.063 g of 4-[4-(decanoylamino)-phenyl]-4-oxo-butyric acid as an off-white solid; MS-(AP+) MH$^+$348.

EXAMPLE 24

4-[4-(3,5-Dimethoxy-benzoylamino)-phenyl]-4-oxo-butyric acid

In a manner similar to that described in Example 3, 3,5-dimethoxy-benzoyl chloride (0.068 g, 0.00034 mol) was allowed to react with 4-(4-amino-phenyl)-4-oxo-butyric acid, methyl ester (0.052 g, 0.00025 mol), and the resulting intermediate was hydrolyzed to give 0.003 g of 4-[4-(3,5-dimethoxy-benzoylamino)-phenyl]-4-oxo-butyric acid as an off-white solid; MS-(AP+) MH$^+$358.

EXAMPLE 25

4-[4-(2-Methoxy-benzoylamino)-phenyl]-4-oxo-butyric acid

In a manner similar to that described in Example 3, 2-methoxy-benzoyl chloride (0.060 g, 0.00035 mol) was allowed to react with 4-(4-amino-phenyl)-4-oxo-butyric acid, methyl ester (0.052 g, 0.00025 mol), and the resulting intermediate was hydrolyzed to give 0.052 g of 4-[4-(2-methoxy-benzoylamino)-phenyl]-4-oxo-butyric acid as an off-white solid; MS-(AP+) MH$^+$328.

EXAMPLE 26

4-[4-(4-Chloro-benzoylamino)-phenyl]-4-oxo-butyric acid

In a manner similar to that described in Example 3, 4-chloro-benzoyl chloride (0.058 g, 0.00033 mol) was allowed to react with 4-(4-amino-phenyl)-4-oxo-butyric acid, methyl ester (0.052 g, 0.00025 mol), and the resulting intermediate was hydrolyzed to give 0.016 g of 4-[4-(4-chloro-benzoylamino)-phenyl]-4-oxo-butyric acid as an off-white solid; MS-(AP+) MH$^+$332.

EXAMPLE 27

4-[4-(4-Methoxy-benzoylamino)-phenyl]-4-oxo-butyric acid

In a manner similar to that described in Example 3, 4-methoxy-benzoyl chloride (0.057 g, 0.00033 mol) was allowed to react with 4-(4-amino-phenyl)-4-oxo-butyric acid, methyl ester (0.052 g, 0.00025 mol), and the resulting intermediate was hydrolyzed to give 0.010 g of 4-[4-(4-methoxy-benzoylamino)-phenyl]-4-oxo-butyric acid as an off-white solid; MS-(AP+) MH$^+$328.

EXAMPLE 28

4-[4-(Benzoylamino)-phenyl]-4-oxo-butyric acid

In a manner similar to that described in Example 3, benzoyl chloride (0.047 g, 0.00033 mol) was allowed to react with 4-(4- amino-phenyl)4-oxo-butyric acid, methyl ester (0.052 g, 0.00025 mol), and the resulting intermediate was hydrolyzed to give 0.040 g of 4-[4-(benzoylamino)-phenyl]-4-oxo-butyric acid as an off-white solid; MS-(AP+) MH$^+$332.

EXAMPLE 29

4-[4-(4-Nitro-benzoylamino)-phenyl]-4-oxo-butyric acid

In a manner similar to that described in Example 3, 4-nitro-benzoyl chloride (0.062 g, 0.00034 mol) was allowed to react with 4-(4-amino-phenyl)-4-oxo-butyric acid, methyl ester (0.052 g, 0.00025 mol), and the resulting intermediate was hydrolyzed to give 0.010 g of 4-[4-(4-nitro-benzoylamino)-phenyl]-4-oxo-butyric acid as a yellow solid; MS-(AP+) MH$^+$343.

EXAMPLE 30

4-[4-(2,4-Difluoro-benzoylamino)-phenyl]-4-oxo-butyric acid

In a manner similar to that described in Example 3, 2,4-difluoro-benzoyl chloride (0.059 g, 0.00033 mol) was allowed to react with 4-(4-amino-phenyl)-4-oxo-butyric acid, methyl ester (0.052 g, 0.00025 mol), and the resulting intermediate was hydrolyzed to give 0.064 g of 4-[4-(2,4-difluoro-benzoylamino)-phenyl]-4-oxo-butyric acid as an off-white solid; MS-(AP+) MH$^+$334.

EXAMPLE 31

4-Oxo-4-[4-(thiophen-2-yl-carbonylamino)-phenyl]-butyric acid

In a manner similar to that described in Example 3, thiophen-2-yl-carbonyl chloride (0.049 g, 0.00033 mol) was allowed to react with 4-(4-amino-phenyl)-4-oxo-butyric acid, methyl ester (0.052 g, 0.00025 mol), and the resulting intermediate was hydrolyzed to give 0.061 g of 4-oxo-4-[4-(thiophen-2-yl-carbonylamino)-phenyl]-butyric acid as a yellow solid; MS-(AP+) MH$^+$304.

EXAMPLE 32

4-[4-(2-Furoylamino)-phenyl]-4-oxo-butyric acid

In a manner similar to that described in Example 3, furoyl chloride (0.044 g, 0.00034 mol) was allowed to react with 4-(4-amino-phenyl)-4-oxo-butyric acid, methyl ester (0.052 g, 0.00025 mol), and the resulting intermediate was hydrolyzed to give 0.033 g of 4-[4-(2-furoylamino)-phenyl]-4-oxo-butyric acid as an off-white solid; MS-(AP+) MH$^+$288.

EXAMPLE 33

4-Oxo-4-[4-(phenyl-acetylamino)-phenyl]-butyric acid

In a manner similar to that described in Example 3, phenyl-acetyl chloride (0.052 g, 0.00034 mol) was allowed to react with 4-(4-amino-phenyl)-4-oxo-butyric acid, methyl ester (0.052 g, 0.00025 mol), and the resulting intermediate was hydrolyzed to give 0.022 g of 4-oxo-4-[4-(phenyl-acetylamino)-phenyl]-butyric acid as an off-white solid; MS-(AP+) MH$^+$312.

EXAMPLE 34

4-Oxo-4-[4-(3-phenyl-propionylamino)-phenyl]-butyric acid

In a manner similar to that described in Example 3, 3-phenyl-propionyl chloride (0.057 g, 0.00034 mol) was allowed to react with 4-(4-amino-phenyl)-4-oxo-butyric acid, methyl ester (0.052 g, 0.00025 mol), and the resulting intermediate was hydrolyzed to give 0.060 g of 4-oxo-4-[4-(3-phenyl-propionylamino)-phenyl]-butyric acid as an off-white solid; MS-(AP+) MH$^+$326.

EXAMPLE 35

4-[4-(3-Carboxy-propionylamino)-phenyl]-4-oxo-butyric acid

In a manner similar to that described in Example 3, 3-carbomethoxy-propionyl chloride (0.051 g, 0.00034 mol) was allowed to react with 4-(4-amino-phenyl)-4-oxo-butyric acid, methyl ester (0.052 g, 0.00025 mol), and the resulting intermediate was hydrolyzed to give 0.020 g of 4-[4-(3-carboxy-propionylamino)-phenyl]-4-oxo-butyric acid as an off-white solid; MS-(AP+) MH$^+$294.

EXAMPLE 36

4-[4-(Carboxy-acetylamino)-phenyl]-4-oxo-butyric acid

In a manner similar to that described in Example 3, carboethoxy-acetyl chloride (0.051 g, 0.00034 mol) was allowed to react with 4-(4-amino-phenyl)-4-oxo-butyric acid, methyl ester (0.052 g, 0.00025 mol), and the resulting intermediate was hydrolyzed to give 0.021 g of 4-[4-(carboxy-acetylamino)-phenyl]-4-oxo-butyric acid as an off-white solid; MS-(AP+) MH$^+$280.

What is claimed is:

1. A compound of Formula I

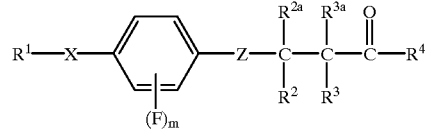

wherein

R$^1$ is hydrogen, alkyl, arylalkyl, or aryl substituted by 1 to 4 substituents selected from the group consisting of alkyl, alkoxy, thioalkoxy, fluorine, bromine, iodine, trifluoromethyl, amino, alkylamino, dialkylamino, nitro, cyano, carboxy, guanidine, amidino, SO$_3$H,

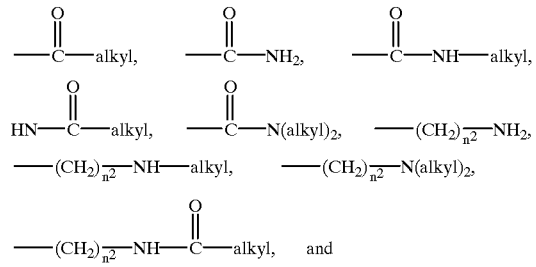

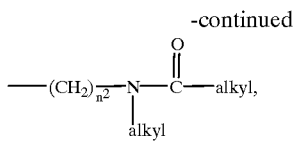

wherein
n² is an integer of 1 to 5;
R², R²ᵃ, R³, and R³ᵃ are either the same of different and are each independently selected from
hydrogen,
fluorine,
—(C$_{1-10}$ alkyl)$_n$—R⁵ wherein n is zero or an integer or 1, alkyl is unsubstituted or optionally substituted with 1 to 3 substituents selected from
—OR⁷ wherein R⁷ is hydrogen or alkyl,
—SR⁷ wherein R⁷ is as defined above,
—CH₂—S—CO-alkyl,

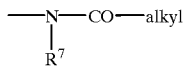

wherein R7 is defined as above,
—CO-alkyl,
—CO₂-alkyl,
—O—CO-alkyl,
—S—CO-alkyl,

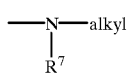

wherein R7 is as defined above,
—SO-alkyl,
—SO₂-alkyl,
—CN,
—CF₃, or
—HN—SO₂-alkyl and,
R⁵ is hydrogen,
aryl,
heteroaryl,
N-phthalimido,
N-2,3-naphthylimido,
indol-3-yl,
imidazol-4-yl,
2-,3-, or 4-pyridyl,
2,4-dioxo-1,5,5-trimethyl-imidazolidin-3-yl or a side chain of a naturally occurring or unnaturally occurring amino acid;
R⁴ is OH;
X is

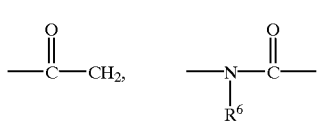

wherein R⁶ is hydrogen, methyl, or optionally R¹ and R⁶ are taken together to form a ring containing from 4 to 7 carbons which may be unsubstituted or substituted with alkyl,
aryl,
arylalkyl,
heteroaryl,
heteroarylalkyl,
heterocycle, or
heterocyclealkyl,

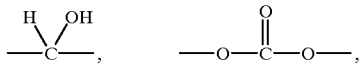

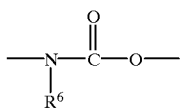

wherein R⁶ is as defined above,

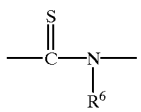

wherein R⁶ is as defined above,

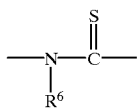

wherein R⁶ is as defined above,

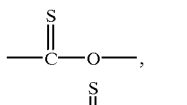

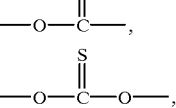

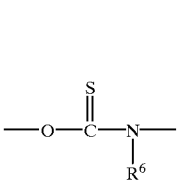

wherein R⁶ is as defined above,

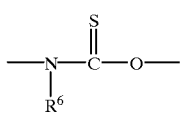

wherein R⁶ is as defined above,

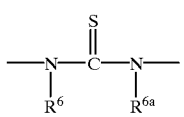

wherein R⁶ is as defined above,

Z is

wherein R⁷ is as defined above,

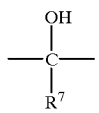

wherein R⁷ is as defined above,

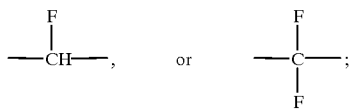

F is fluorine; and m is zero or an integer of 1 to 4; and corresponding isomers thereof; or a pharmaceutically acceptable salt thereof.

2. The compound according to claim 1 wherein X is

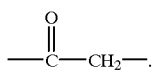

3. The compound according to claim 1 wherein X is

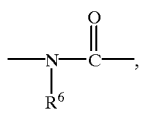

wherein $R^6$ is hydrogen, methyl, or optionally $R^1$ and $R^6$ are taken together to form a ring containing from 4 to 7 carbons which may be unsubstituted or substituted with alkyl, aryl, arylalkyl, heteroaryl, heteroarylalkyl, heterocycle, or heterocyclealkyl.

4. The compound according to claim 1 wherein X is

5. The compound according to claim 1 wherein X is

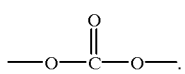

6. The compound according to claim 1 wherein X is

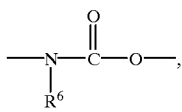

wherein $R^6$ is hydrogen, methyl, or optionally $R^1$ and $R^6$ are taken together to form a ring containing from 4 to 7 carbons which may be unsubstituted or substituted with alkyl, aryl, arylalkyl, heteroaryl, heteroarylalkyl, heterocycle, or heterocyclealkyl.

7. The compound according to claim 1 wherein X is

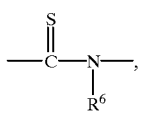

wherein $R^6$ is hydrogen, methyl, or optionally $R^1$ and $R^6$ are taken together to form a ring containing from 4 to 7 carbons which may be unsubstituted or substituted with alkyl, aryl, arylalkyl, heteroaryl, heteroarylalkyl, heterocycle, or heterocyclealkyl.

8. The compound according to claim 1 wherein X is

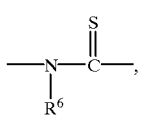

wherein $R^6$ is hydrogen, methyl, or optionally $R^1$ and $R^6$ are taken together to form a ring containing from 4 to 7 carbons which may be unsubstituted or substituted with alkyl, aryl, arylalkyl, heteroaryl, heteroarylalkyl, heterocycle, or heterocyclealkyl.

9. The compound according to claim 1 wherein

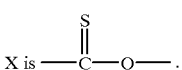

10. The compound according to claim 1 wherein

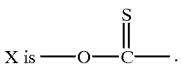

11. The compound according to claim 1 wherein

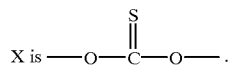

12. The compound according to claim 1 wherein X is

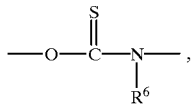

wherein $R^6$ is hydrogen, methyl, or optionally $R^1$ and $R^6$ are taken together to form a ring containing from 4 to 7 carbons which may be unsubstituted or substituted with alkyl, aryl, arylalkyl, heteroaryl, heteroarylalkyl, heterocycle, or heterocyclealkyl.

13. The compound according to claim 1 wherein X is

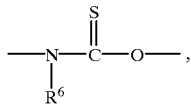

wherein $R^6$ is hydrogen, methyl, or optionally $R^1$ and $R^6$ are taken together to form a ring containing from 4 to 7 carbons which may be unsubstituted or substituted with alkyl, aryl, arylalkyl, heteroaryl, heteroarylalkyl, heterocycle, or heterocyclealkyl.

14. The compound according to claim 1 wherein X is

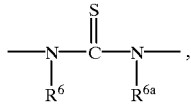

wherein $R^6$ and $R^{6a}$ are either the same or different and are each independently as defined for $R^6$, wherein $R^6$ is hydrogen, methyl, or optionally $R^1$ and $R^6$ are taken together to form a ring containing from 4 to 7 carbons which may be unsubstituted or substituted with alkyl, aryl, arylalkyl, heteroaryl, heteroarylalkyl, heterocycle, or heterocyclealkyl.

15. The compound according to claim 1 wherein

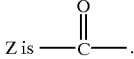

16. The compound according to claim 1 wherein

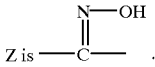

17. The compound selected from the group consisting of:
4-[4-(4-Bromo-benzoylamino)-phenyl]-4-oxo-butyric acid;
4-(4-Benzoylamino-phenyl)-4-oxo-butyric acid;
4-[4-(2-Fluoro-benzoylamino)-phenyl]-4-oxo-butyric acid;
4-[4-(3-Fluoro-benzoylamino)-phenyl]-4-oxo-butyric acid;
4-[4-(4-Fluoro-benzoylamino)-phenyl]-4-oxo-butyric acid;
4-[4-(2-Iodo-benzoylamino)-phenyl]-4-oxo-butyric acid;
4-[4-(2,4-Dichloro-benzoylamino)-phenyl]-4-oxo-butyric acid;
4-[4-(2,6-Dichloro-benzoylamino)-phenyl]-4-oxo-butyric acid;
4-[4-(3,4-Dichloro-benzoylamino)-phenyl]-4-oxo-butyric acid;
4-[4-(2,4-Difluoro-benzoylamino)-phenyl]-4-oxo-butyric acid;
4-[4-(4-(4-Bromo-phenyl)-butyrylamino)-phenyl]-4-oxo-butyric acid;
4-[4-(4-(4-Bromo-phenyl)-acetylamino)-phenyl]-4-oxo-butyric acid;
4-[4-(3-Cyano-benzoylamino)-phenyl]-4-oxo-butyric acid;
4-[4-(Benzo[1,3]diozol-5-yl-carbonylamino)-phenyl]-4-oxo-butyric acid;
4-[4-(Biphenyl-4-yl-carbonylamino)-phenyl]-4-oxo-butyric acid;
4-[4-(4-Cyano-benzoylamino)-phenyl]-4-oxo-butyric acid;
4-[4-(2-Methoxy-benzoylamino)-phenyl]-4-oxo-butyric acid;
4-[4-(3-Methoxy-benzoylamino)-phenyl]-4-oxo-butyric acid;
4-[4-(4-Methoxy-benzoylamino)-phenyl]-4-oxo-butyric acid;
4-[4-(2,4-Dimethoxy-benzoylamino)-phenyl]-4-oxo-butyric acid;
4-[4-(2,5-Dimethoxy-benzoylamino)-phenyl]-4-oxo-butyric acid;
4-[4-(2,6-Dimethoxy-benzoylamino)-phenyl]-4-oxo-butyric acid;
4-[4-(3,5-Dimethoxy-benzoylamino)-phenyl]-4-oxo-butyric acid;
4-Oxo-4-[4-(3,4,5-trimethoxy-benzoylamino)-phenyl]-butyric acid;
4-[4-(4-Methyl-benzoylamino)-phenyl]-4-oxo-butyric acid;
4-[4-(4-Decyl-benzoylamino)-phenyl]-4-oxo-butyric acid;
4-[4-(4-Ethyl-benzoylamino)-phenyl]-4-oxo-butyric acid;
4-[4-(4-Tert-Butyl-benzoylamino)-phenyl]-4-oxo-butyric acid;
4-[4-(4-Butoxy-benzoylamino)-phenyl]-4-oxo-butyric acid;
4-[4-(Cyclohexanecarbonyl-amino)-phenyl]-4-oxo-butyric acid;
4-Oxo-4-[4-(phenylacetyl-amino)-phenyl]-butyric acid;
4-Oxo-4-[4-(3-phenyl-propionyl-amino)-phenyl]-butyric acid;
4-[-4-(Dodecanoyl-amino)-phenyl]-4-oxo-butyric acid;
4-[-4-(Heptanoyl-amino)-phenyl]-4-oxo-butyric acid;
4-[4-(3-Nitro-benzoylamino)-phenyl]-4-oxo-butyric acid;
4-[4-(4-Nitro-benzoylamino)-phenyl]-4-oxo-butyric acid;
4-[4-(Butyryl-amino)-phenyl]-4-oxo-butyric acid;
4-[-4-(Decanoyl-amino)-phenyl]-4-oxo-butyric acid;
4-[4-(4-Chloro-phenoxy-acetylamino)-phenyl]-4-oxo-butyric acid;
4-[4-(3,4-Dimethoxy-benzoylamino)-phenyl]-4-oxo-butyric acid;
4-[4-(3,4-Dimethoxy-phenylacetyl-amino)-phenyl]-4-oxo-butyric acid;
4-[4-(Naphthyl-2-yl-carbonylamino)-phenyl]-4-oxo-butyric acid;
4-[4-(Adamantan-1-yl-carbonylamino)-phenyl]-4-oxo-butyric acid;
4-[4-(Oleoyl-amino)-phenyl]-4-oxo-butyric acid;
4-[4-(Nonanoyl-amino)-phenyl]-4-oxo-butyric acid;
4-Oxo-4-[4-(propionylamino)-phenyl]-butyric acid;
4-Oxo-4-[4-(phenoxy-acetylamino)-phenyl]-butyric acid;
4-[4-(Oxalamino)-phenyl]-4-oxo-butyric acid;
4-[4-(4-Chloro-3-nitro-benzoylamino)-phenyl]-4-oxo-butyric acid;
4-Oxo-4[4-(phenylazo-benzoylamino)-phenyl]-butyric acid;
4-[4-(Cinnamoylamino)-phenyl]-4-oxo-butyric acid;

(±)-2-(Acetylthio)methyl-4-[4-(4-methyl-benzoylamino)-phenyl]-4-oxo-butyric acid;
(±)-3-(Acetylthio)methyl-4-[4-(4-methyl-benzoylamino)-phenyl]-4-oxo-butyric acid;
(±)-2-(2,4-Dioxo-1,5,5-trimethyl-imidazolidin-3-yl)methyl-4-[4-(4-methyl-benzoylamino)-phenyl]-4-oxo-butyric acid;
(±)-2-(4-Benzyloxy-phenyl)methyl-4-[4-(4-methyl-benzoylamino)-phenyl]-4-oxo-butyric acid;
(±)-4-[4-(4-Methyl-benzoylamino)-phenyl]-4-oxo-2-(3-phenyl-propyl)-butyric acid;
(±)-4-[4-(4-Methyl-benzoylamino)-phenyl]-4-oxo-2-(2-phthalimido-ethyl)-butyric acid;
(±)-2-(4-Methyl-benzenesulfonyl)amino-4-[4-(4-methyl-benzoylamino)-phenyl]-4-oxo-butyric acid;
(±)-4-[4-(4-Methyl-benzoylamino)-phenyl]-4-oxo-3-(pyridin-3-yl)methyl-butyric acid;
4-[4-(Octanoylamino)-phenyl]-4-oxo-butyric acid;
4-[4-(4-Heptyl-benzoylamino)-phenyl]-4-oxo-butyric acid;
4-[4-(2-Naphthoylamino)-phenyl]-4-oxo-butyric acid;
4-Oxo-4-[4-(4-trifluoromethyl-benzoylamino)-phenyl]-butyric acid;
4-Oxo-4-[4-(2,3,4,5,6-pentafluoro-benzoylamino)-phenyl]-butyric acid;
4-[4-(2-Fluoro4-trifluoromethyl-benzoylamino)-phenyl]-4-oxo-butyric acid;
4-[4-(3-Fluoro-4-trifluoromethyl-benzoylamino)-phenyl]-4-oxo-butyric acid;
4-[4-(4-Hexyloxy-benzoylamino)-phenyl]-4-oxo-butyric acid;
4-[4-(4-Dipropylaminosulfonyl-benzoylamino)-phenyl]-4-oxo-butyric acid;
4-Oxo-[4-3-phenyl-ureido)-phenyl]-butyric acid;
{4-[3-(4-Chloro-phenyl)-ureido]-phenyl}-4-oxo-butyric acid;
{4-[3-(4-Bromo-phenyl)-ureido]-phenyl}-4-oxo-butyric acid;
{4-[3-(4-Fluoro-phenyl)-ureido]-phenyl}-4-oxo-butyric acid;
4-Oxo-{4-[3-(4-trifluoro-phenyl)-ureido]-phenyl}-butyric acid
{4-[3-(4-Methoxy-phenyl)-ureido]-phenyl}-4-oxo-butyric acid;
{4-[3-(4-Methyl-phenyl)-ureido]-phenyl}-4-oxo-butyric acid;
4-Oxo-4-(4-[phenoxycarbonylamino)-phenyl]-butyric acid;
4-{4-[(4-Chloro-phenoxy)-carbonylamino]-phenyl}-4-oxo-butyric acid;
4-{4-[(4-Bromo-phenoxy)-carbonylamino]-phenyl}-4-oxo-butyric acid;
4-{4-[(4-Fluoro-phenoxy)-carbonylamino]-phenyl}-4-oxo-butyric acid;
4-{4-[(4-Methoxy-phenoxy)-carbonylamino]-phenyl}-4-oxo-butyric acid;
4-{4-[(4-Methyl-phenoxy)-carbonylamino]-phenyl}-4-oxo-butyric acid;
4-Oxo-4-{4-[(4-trifluoromethyl-phenoxy)-carbonylamino]-phenyl}-butyric acid;
4-[4-(4-Bromo-benzoylamino)phenyl]-4-hydroxyimino-butyric acid;
4-[4-Benzoylamino-phenyl)-4-hydroxyimino-butyric acid
4-[4-(4-Chloro-benzoylamino)-phenyl]-4-hydroxyimino-butyric acid;
4-[4-(2-Fluoro-benzoylamino)-phenyl]-4-hydroxyimino-butyric acid;
4-[4-(3-Fluoro-benzoylamino)-phenyl]-4-hydroxyimino-butyric acid;
4-[4-(4-Fluoro-benzoylamino)-phenyl]-4-hydroxyimino-butyric acid;
4-Hydroxyimino-4-[4-(2-iodo-benzoylamino)-phenyl]-butyric acid;
4-[4-(2,4-Dichloro-benzoylamino)-phenyl]-4-hydroxyimino-butyric acid;
4-[4-(2,6-Dichloro-benzoylamino)-phenyl]-4-hydroxyimino-butyric acid;
4-[4-(3,4-Dichloro-benzoylamino)-phenyl]-4-hydroxyimino-butyric acid;
4-[4-(2,4-Difluoro-benzoylamino)-phenyl]-4-hydroxyimino-butyric acid;
4-[4-(4-(4-Bromo-phenyl)-butyrylamino)-phenyl]-4-hydroxyimino-butyric acid;
4-[4-(4-(4-Bromo-phenyl)-acetylamino)-phenyl]-4-hydroxyimino-butyric acid;
4-[4-(3-Cyano-benzoylamino)-phenyl]-4-hydroxyimino-butyric acid
4-[4-(Benzo[1,3]dioxol-5-yl-carbonylamino)-phenyl]-4-hydroxyimino-butyric acid
4-[4-(Biphenyl-4-yl-carbonylamino)-phenyl]-4-hydroxyimino-butyric acid;
4-[4-(4-Cyano-benzoylamino)-phenyl]-4-hydroxyimino-butyric acid
4-Hydroxyimino-4-[4-(2-methoxy-benzoylamino)-phenyl]-butyric acid;
4-Hydroxyimino-4-[4-(3-methoxy-benzoylamino)-phenyl]-butyric acid;
4-Hydroxyimino-4-[4-(4-methoxy-benzoylamino)-phenyl]-butyric acid;
4-[4-(2,4-Dimethoxy-benzoylamino)-phenyl]-4-hydroxyimino-butyric acid;
4-[4-(2,5-Dimethoxy-benzoylamino)-phenyl]-4-hydroxyimino-butyric acid;
4-[4-(2,6-Dimethoxy-benzoylamino)-phenyl]-4-hydroxyimino-butyric acid;
4-[4-(3,5-Dimethoxy-benzoylamino)-phenyl]-4-hydroxyimino-butyric acid;
4-Hydroxyimino-4-[4-(3,4,5-trimethoxy-benzoylamino)-phenyl]-butyric acid;
4-Hydroxyimino-4-[4-(4-Methyl-benzoylamino)-phenyl]-butyric acid;
4-[4-(4-Decyl-benzoylamino)phenyl]-4-hydroxyimino-butyric acid;
4-[4-(4-Ethyl-benzoylamino)phenyl]-4-hydroxyimino-butyric acid;
4-[4-(4-Tert-Butyl-benzoylamino)phenyl]-4-hydroxyimino-butyric acid;
4-[4-(4-Butoxy-benzoylamino)phenyl]-4-hydroxyimino-butyric acid;
4-[4-(Cyclohexanecarbonyl-amino)phenyl]-4-hydroxyimino-butyric acid;
4-Hydroxyimino-4-[4-(phenylacetyl-amino)-phenyl]-butyric acid;
4-Hydroxyimino-4-[4-(3-phenyl-propionyl-amino)-phenyl]-butyric acid;
4-[4-(2,2-Dimethyl-pentanoyl-amino)-phenyl]-4-hydroxyimino-butyric acid;
4-[4-(Dodecanoyl-amino)-phenyl]-4-hydroxyimino-butyric acid;
4-[4-(Heptanoyl-amino)-phenyl]-4-hydroxyimino-butyric acid;
4-Hydroxyimino-4-[4-(3-nitro-benzoylamino)-phenyl]-butyric acid;
4-Hydroxyimino-4-[4-(4-nitro-benzoylamino)-phenyl]-butyric acid;
4-[4-(Butyryl-amino)-phenyl]-4-hydroxyimino-butyric acid;

4-[4-(Decanoyl-amino)-phenyl]-4-hydroxyimino-butyric acid;
4-[4-(Diphenylacetyl-amino)-phenyl]-4-hydroxyimino-butyric acid;
4-[4-(4-Chloro-phenoxy-acetylamino)-phenyl]-4-hydroxyimino-butyric acid;
4-[4-(3,4-Dimethoxy-benzoylamino)-phenyl]-4-hydroxyimino-butyric acid;
4-[4-(3,4-Dimethoxy-phenylacetyl-amino)-phenyl]-4-hydroxyimino-butyric acid;
4-Hydroxyimino-4-[4-(naphthyl-2-yl-carbonylamino)-phenyl]-butyric acid;
4-[4-(Adamantan-1-yl-carbonylamino)-phenyl]-4-hydroxyimino-butyric acid;
4-Hydroxyimino-4-[4-(oleoyl-amino)-phenyl]-butyric acid;
4-Hydroxyimino-4-[4-(nonanoyl-amino)-phenyl]-butyric acid;
4-Hydroxyimino-4-[4-(propionylamino)-phenyl]-butyric acid;
4-Hydroxyimino-4-[4-(2-phenoxy-propionylamino)-phenyl]-butyric acid;
4-Hydroxyimino-4-[4-(phenoxy-acetylamino)-phenyl]-butyric acid;
4-Hydroxyimino-4-[4-(oxalamino)-phenyl]-butyric acid;
4-[4-(4-Chloro-3-nitro-benzoylamino)-phenyl]-4-hydroxyimino-butyric acid;
4-Hydroxyimino-4-[4-(phenylazo-benzoylamino)-phenyl]-butyric acid;
4-[4-(Cinnamoylamino)-phenyl]-4-hydroxyimino-butyric acid;
(±)-2-(Acetylthio)methyl-4-Hydroxyimino-4-[4-(4-methyl-benzoylamino)-phenyl]-butyric acid;
(±)-3-(Acetylthio)methyl-4-hydroxyimino-4-[4-(4-methyl-benzoylamino)-phenyl]-butyric acid;
(±)-2-(2,4-Dioxo-1,5,5-trimethyl-imidazolidin-3-yl)methyl-4-hydroxyimino-4-[4-(4-methyl-benzoylamino)-phenyl]-butyric acid;
(±)-2-(4-Benzyloxy-phenyl)methyl-4-hydroxyimino-4-[4-(4-methyl-benzoylamino)-phenyl]-butyric acid;
(±)-4-Hydroxyimino-4-[4-(4-methyl-benzoylamino)-phenyl]-2-(3-phenyl-propyl)-butyric acid;
(±)-4-Hydroxyimino-4-[4-(4-methyl-benzoylamino)-phenyl]-2-(2-phthalimido-ethyl)-butyric acid;
(±)-4-Hydroxyimino-2-(4-methyl-benzenesulfonyl)amino-4-[4-(4-methyl-benzoylamino)-phenyl]-butyric acid; and
(±)-4-Hydroxyimino-4-[4-(4-methyl-benzoylamino)-phenyl]-3-(pyridin-3-yl)methyl-butyric acid;
and corresponding isomers thereof; or a pharmaceutically acceptable salt thereof.

18. The method of inhibiting a matrix metalloproteinase comprising administering to a host suffering therefrom a therapeutically effective amount of a compound according to claim 1 in unit dosage form.

19. The method of inhibiting gelatinase A comprising administering to a host suffering therefrom a therapeutically effective amount of a compound according to claim 1 in unit dosage form.

20. The method of inhibiting stromelysin-1 comprising administering to a host suffering therefrom a therapeutically effective amount of a compound according to claim 1 in unit dosage form.

21. The method of inhibiting collagenase-3 comprising administering to a host suffering therefrom a therapeutically effective amount of a compound according to claim 1 in unit dosage form.

22. A pharmaceutical composition comprising a compound according to claim 1 in admixture with a pharmaceutically acceptable excipient, diluent, or carrier.

23. A pharmaceutical composition comprising a therapeutically effective amount of a compound according to claim 1 in admixture with a pharmaceutically acceptable excipient, diluent, or carrier.

24. A compound of Formula I

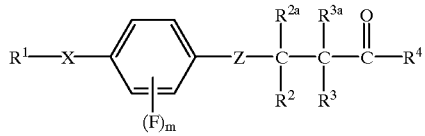

wherein $R^1$ is $C_2$–$C_8$ alkyl, arylalkyl, aryl substituted by 1 to 4 substituents selected from the group consisting of alkyl, alkoxy, thioalkoxy, fluorine, bromine, iodine, trifluoromethyl, amino, alkylamino, dialkylamino, nitro, cyano, carboxy, amidino, $SO_3H$,

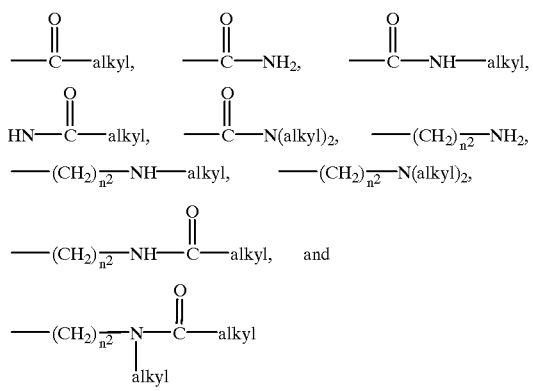

wherein $n^2$ is an integer of 1 to 5, or a saturated hydrocarbon ring having 4 to 8 carbon atoms;

$R^2$, $R^{2a}$, $R^3$, and $R^{3a}$ are either the same of different and are each independently selected from hydrogen, fluorine, —$(C_{1-10}$ alkyl$)_n$—$R^5$ wherein n is zero or an integer or 1, alkyl is unsubstituted or optionally substituted with 1 to 3 substituents selected from —$OR^7$ wherein $R^7$ is hydrogen or alkyl, —$SR^7$ wherein $R^7$ is as defined above, —$CH_2$—S—CO-alkyl,

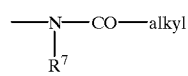

wherein R7 is defined as above,

—CO-alkyl,

—$CO_2$-alkyl,

—O—CO-alkyl,
—S—CO-alkyl,

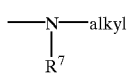

wherein R7 is as defined above,
—SO-alkyl,
—SO₂-alkyl,
—CN,
—CF₃, or
—HN—SO₂-alkyl and, R⁵ is hydrogen,
aryl,
heteroaryl,
N-phthalimido,
N-2,3-naphthylimido,
indol-3-yl,
imidazol-4-yl,
2-,3-, or 4-pyridyl,
2,4-dioxo-1,5,5-trimethyl-imidazolidin-3-yl or a side chain of a naturally occurring or unnaturally occurring amino acid;

R⁴ is OH;

X is

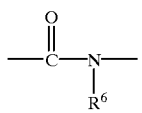

wherein R⁶ is hydrogen, methyl, or optionally R¹ and R⁶ are taken together to form a ring containing from 4 to 7 carbons which may be unsubstituted or substituted with alkyl,
aryl,
arylalkyl,
heteroaryl,
heteroarylalkyl,
heterocycle, or
heterocyclealkyl,

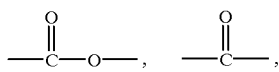

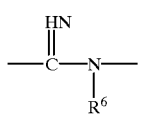

wherein R⁶ is as defined above,

Z is

wherein R⁷ is as defined above,

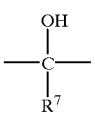

wherein R⁷ is as defined above,

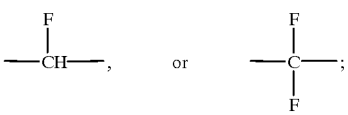

F is fluorine; and
m is zero or an integer of 1 to 4; and corresponding isomers thereof; or pharmaceutically acceptable salt thereof.

25. The compound of claim 24, wherein Z is

26. The method of inhibiting a matrix metalloproteinase comprising administering to a host suffering therefrom a therapeutically effective amount of a compound according to claim 24 in unit dosage form.

27. The method of inhibiting gelatinase A comprising administering to a host suffering therefrom a therapeutically effective amount of a compound according to claim 24 in unit dosage form.

28. The method of inhibiting stromelysin-1 comprising administering to a host suffering therefrom a therapeutically effective amount of a compound according to claim 24 in unit dosage form.

29. The method of inhibiting collagenase3 comprising administering to a host suffering therefrom a therapeutically effective amount of a compound according to claim 24 in unit dosage form.

30. A pharmaceutical composition comprising a compound according to claim 24 in admixture with a pharmaceutically acceptable excipient, diluent, or carrier.

31. A pharmaceutical composition comprising a therapeutically effective amount of a compound according to claim 24 in admixture with a pharmaceutically acceptable excipient, diluent, or carrier.

32. A compound of Formula I

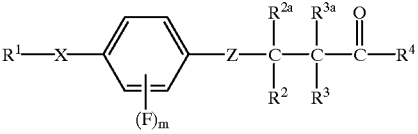

wherein
R¹ is hydrogen,
alkyl,
arylalkyl,
aryl substituted by 1 to 4 substituents selected from the group consisting of alkyl, alkoxy, thioalkoxy, fluorine, bromine, iodine, trifluoromethyl, amino, alkylamino, dialkylamino, nitro, cyano, carboxy, guanidine, amidino, SO₃H,

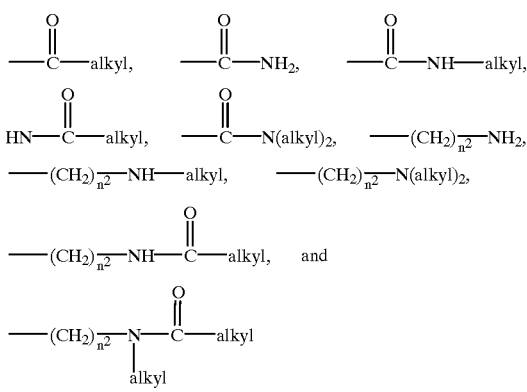

wherein n² is an integer of 1 to 5, or
a saturated hydrocarbon ring having 4 to 8 carbon atoms;
$R^2$, $R^{2a}$, $R^3$, and $R^{3a}$ are either the same of different and are each independently selected from
hydrogen,
fluorine,
—$(C_{1-10}$ alkyl$)_n$—$R^5$ wherein n is zero or an integer or 1, alkyl is unsubstituted or optionally substituted with 1 to 3 substituents selected from
—$OR^7$ wherein $R^7$ is hydrogen or alkyl,
—$SR^7$ wherein $R^7$ is as defined above,
—$CH_2$—S—CO-alkyl,

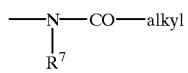

wherein R7 is defined as above,
—CO-alkyl,
—CO₂-alkyl,
—O—CO-alkyl,
—S—CO-alkyl,

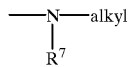

wherein R7 is as defined above,
—SO-alkyl,
—SO₂-alkyl,
—CN,
—CF₃, or
—HN—SO₂-alkyl and,
$R^5$ is hydrogen,
aryl,
hereroaryl,
N-phthalimido,
N-2,3-naphthylimido,
indol-3-yl,
imidazol-4-yl,
2-,3-, or 4-pyridyl,
2,4-dioxo-1,5,5-trimethyl-imidazolidin-3-yl or a side chain of a naturally occurring or unnaturally occurring amino acid;

$R^4$ is OH;
X is

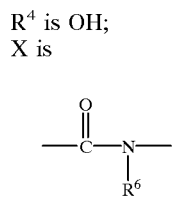

wherein $R^6$ is hydrogen, methyl, or optionally $R^1$ and $R^6$ are taken together to form a ring containing from 4 to 7 carbons which may be unsubstituted or substituted with alkyl,
aryl,
arylalkyl,
hereroaryl,
heteroarylalkyl,
heterocycle, or
heterocyclealkyl,
Z is

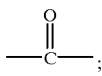

F is fluorine; and
m is zero or an integer of 1 to 4; and corresponding isomers thereof, or a pharmaceutically acceptable salt thereof.

33. The method of inhibiting a matrix matalloproteinase comprising administering to a host suffering therefrom a therapeutically effective amount of a compound according to claim 32 in unit dosage form.

34. The method of inhibiting gelatinase A comprising administering to a host suffering therefrom therapeutically effective amount of a compound according to claim 32 in unit dosage form.

35. The method of inhibiting stromelysin-1 comprising administering to a host suffering therefrom a therapeutically effective amount of a compound according to claim 32 in unit dosage form.

36. The method of inhibiting collagenase-3 comprising administering to a host suffering therefrom a therapeutically effective amount of a compound according to claim 32 in unit dosage form.

37. A pharmaceutical composition comprising a compound according to claim 32 in admixture with a pharmaceutically acceptable excipient, diluent, or carrier.

38. A pharmaceutical composition comprising a therapeutically effective amount of a compound according to claim 32 in admixture with a pharmaceutically acceptable excipient, diluent, or carrier.

39. The compound
4-[4-(3-Carboxy-propionyl-amino)-phenyl]-4-oxo-butyric acid;
4-[4-(4-Carboxy-butyryl-amino)-phenyl]-4-oxo-butyric acid;
4-[4-(4-Carboxy-acetyl-amino)-phenyl]-4-oxo-butyric acid;
4-[4-(2-Acetoxy-2,2-dimethyl-acetylamino)-phenyl]-4-oxo-butyric acid;
4-[4-(3-Carboxy-propionyl-amino)-phenyl]-4-hydroxyimino-butyric acid;
4-[4-(4-Carboxy-butyryl-amino)-phenyl]-4-hydroxyimino-butyric acid;
4-[4-(4-Carboxy-acetyl-amino)-phenyl]-4-hydroxyimino-butyric acid; or
4-[4-(2-Acetoxy-2,2-dimethyl-acetylamino)-phenyl]-4-oxo-butyric acid.

* * * * *

UNITED STATES PATENT AND TRADEMARK OFFICE
CERTIFICATE OF CORRECTION

PATENT NO.    : 6,541,521 B1
DATED         : April 1, 2003
INVENTOR(S)   : Purchase, Jr. et al.

It is certified that error appears in the above-identified patent and that said Letters Patent is hereby corrected as shown below:

<u>Title page,</u>
Item [56], OTHER PUBLICATIONS,
1st reference, "Hampel et al.", "Hsmpel" should read -- Hampel --
2nd reference, "Tyagi et al.", "collegenase in falling" should read -- collagenase in failing --
3rd reference, "Andrews", "within cartilage" should read -- within articular cartilage --
4th reference, "Lee et al.", "faliure" should read -- failure --
6th reference, "Lovette et al.", "end enhanced expression in a model on" should read -- and enhanced expression in a model of --
10th reference, "DeClerck", insert title and reference -- "Inhibition of Invasion and Metastasis in Cells Transfected with an Inhibitor of Metalloproteinases," *Cancer Research*, 1992;52:701-8 --
11th reference, "Freije et al.", in order to separate from the "DeClerck" reference, please insert paragraph before the "Freije" reference.
13th reference, "Galis et al.", "degarding" should read -- degrading --
Last reference, "Taraboletti et al.", "mixture metalloproproteinases" should read -- matrix metalloproteinases --

<u>Column 68,</u>
Line 39, "collagenase3" should read -- collagenase-3 --

<u>Column 69,</u>
Line 58, "hereroaryl" should read -- heteroaryl --

<u>Column 70,</u>
Line 16, "hereroaryl" should read -- heteroaryl --

Signed and Sealed this

Second Day of March, 2004

JON W. DUDAS
*Acting Director of the United States Patent and Trademark Office*